(12) United States Patent
Schröder et al.

(10) Patent No.: US 11,726,090 B2
(45) Date of Patent: Aug. 15, 2023

(54) MEANS AND METHODS FOR DIAGNOSING PANCREATIC CANCER

(71) Applicants: Deutsches Krebsforschungszentrum, Heidelberg (DE); Queen Mary University of London, London (GB)

(72) Inventors: Christoph Schröder, Heidelberg (DE); Jörg Hoheisel, Wiesloch (DE); Tatjana Crnogorac-Jurcevic, Chislehurst (GB)

(73) Assignees: DEUTSCHES KREBSFORSCHUNGSZENTRUM, Heidelberg (DE); QUEEN MARY UNIVERSITY OF LONDON, London (GB)

( * ) Notice: Subject to any disclaimer, the term of this patent is extended or adjusted under 35 U.S.C. 154(b) by 0 days.

(21) Appl. No.: 15/387,233

(22) Filed: Dec. 21, 2016

(65) Prior Publication Data

US 2017/0168062 A1    Jun. 15, 2017

Related U.S. Application Data

(62) Division of application No. 13/576,912, filed as application No. PCT/EP2011/052182 on Feb. 15, 2011, now Pat. No. 9,551,035.

(30) Foreign Application Priority Data

Feb. 17, 2010   (EP) ..................... 10001596

(51) Int. Cl.
    G01N 33/574    (2006.01)
    C12Q 1/6886    (2018.01)
    G01N 33/53     (2006.01)

(52) U.S. Cl.
    CPC ..... *G01N 33/57438* (2013.01); *C12Q 1/6886* (2013.01); *G01N 33/5302* (2013.01); *C12Q 2600/158* (2013.01)

(58) Field of Classification Search
    CPC combination set(s) only.
    See application file for complete search history.

(56) References Cited

U.S. PATENT DOCUMENTS

| | | | |
|---|---|---|---|
| 5,744,305 A | 8/1998 | Fodor et al. | |
| 2004/0219572 A1* | 11/2004 | Chen | G01N 33/57438 435/6.14 |
| 2005/0129697 A1 | 6/2005 | Emtage | |
| 2005/0158324 A1 | 7/2005 | Emtage | |
| 2005/0260639 A1* | 11/2005 | Nakamura | C12Q 1/6886 435/6.14 |
| 2006/0019256 A1 | 1/2006 | Clarke et al. | |
| 2007/0105133 A1* | 5/2007 | Clarke | C12N 5/0693 435/6.12 |
| 2008/0075722 A1 | 3/2008 | DePinho et al. | |
| 2010/0105571 A1* | 4/2010 | Borrebaeck | G01N 33/57438 506/9 |
| 2010/0196426 A1* | 8/2010 | Skog | C12Q 1/6886 604/7 |
| 2011/0008914 A1* | 1/2011 | Yeung | C12Q 1/6886 436/518 |
| 2011/0294136 A1* | 12/2011 | Meyer | G01N 33/57438 435/7.1 |

FOREIGN PATENT DOCUMENTS

| | | |
|---|---|---|
| WO | WO 2009/092108 A2 | 7/2009 |
| WO | WO 2010/028098 A2 | 3/2010 |

OTHER PUBLICATIONS

Bernstorff et al, Cancer, 94:2552-2560, 2002.*
Koizumi et al., "New Monoclonal 1C5, Reactive with Human Cervical Adenocarcinoma of the Uterus, with Immunodiagnostic Potential," *Cancer Research*, vol. 48, pp. 6565-6572 (1988).
Baba et al., "Cloning and Characterization of a Tumor-Associated Antigen, β-Casein-like Protein," *Biochem. And Biophy. Res. Communications*, vol. 284, pp. 340-345 (2001).
Jemal et al., "Cancer Statistics," *CA Cancer J. Clin.*, vol. 59, pp. 225-249 (2009).
Needleman et al., "A General Method Applicable to the Search for Similarities in the Amino Acid Sequence of Two Proteins," *J. Mol. Biol.*, vol. 48, pp. 443-453 (1970).
Remy et al., "Regulation of Apoptosis by the Ft1 Protein, a New Modulator of Protein Kinase B/Akt," *Molecular and Cellular Biology*, pp. 1493-1504 (2004).
Goggins, "Molecular Markers of Early Pancreatic Cancer," *Journ. Of Clin. Oncology*, vol. 23, No. 20, pp. 4524-4531(2005).
Pulli et al., "One-Step Homogeneous Immunoassay for Small Analytes," *Anal. Chem.*, vol. 77, pp. 2637-2642 (2005).
Weeks et al., "Analysis of the Urine Proteome in Patients with Pancreatic Ductal Adenocarcinoma," *Proteomics Clin. Appl.*, vol. 2, pp. 1047-1057 (2008).
Nolan et al., "Suspension Array Technology: evolution of the Flat-Array Paradigm," *TRENDS in Biotechnology*, vol. 20, No. 1, pp. 9-12 (2002).
Smith et al., "Comparison of Biosequences," *Advances in Applied Mathematics*, vol. 2, pp. 482-489 (1981).

(Continued)

*Primary Examiner* — Mark Halvorson
(74) *Attorney, Agent, or Firm* — Foley & Lardner LLP

(57) ABSTRACT

The present invention pertains to the field of cancer diagnosis. Specifically, it relates to a method for diagnosing pancreas cancer in a subject comprising the steps of determining in a sample of a subject suspected to suffer from pancreas cancer the amount of at least one biomarker selected from the biomarkers shown in Table 1 and comparing the said amount of the at least one biomarker with a reference, whereby pancreas cancer is to be diagnosed. The present invention also contemplates a method for identifying whether a subject is in need of a pancreas cancer therapy comprising the steps of the aforementioned methods and the further step of identifying a subject in need of a pancreas cancer therapy if said subject is to be diagnosed to suffer from pancreas cancer. Contemplated are, furthermore, diagnostic devices and kits for carrying out said methods.

16 Claims, No Drawings

Specification includes a Sequence Listing.

(56) References Cited

OTHER PUBLICATIONS

Feng et al., "Progressive Sequence Alignment as a Prerequisite to Correct Phylogenetic Trees," *J. Mol. Evol.*, vol. 25, pp. 351-360 (1987).

Higgins et al., "Fast and Sensitive Multiple Sequence Alignments on a Microcomputer," vol. 5, pp. 151-153 (1989).

Melstrom et al., "Apigenin Inhibits the GLUT-1 Glucose Transporter and the Phosphoinositide 3-Kinase/Akt Pathway in Human Pancreatic Cancer Cells," *Pancreas*, vol. 37, pp. 426-431 (2008).

Fredriksson et al., "Protein Detection Using Proximity-Dependent DNA Ligation Assays," *Nature Biotechnology*, vol. 20, pp. 473-477 (2002).

International Preliminary Report on Patentability issued in related International Patent Application No. PCT/EP2011/52182, dated Aug. 30, 2012.

International Search Report and Written Opinion issued in related International Patent Application No. PCT/EP2011/052182, dated Mar. 15, 2011.

Treiber et al., "Keratin 8 sequence variants in patients with pancreatitis and pancreatic cancer," *J. Mol. Med.*, vol. 84, pp. 1015-1022 (2006).

Dhillon et al., "MAP Kinase Signalling Pathways in Cancer," *Oncogene*, vol. 26, pp. 3279-3290 (2007).

Cao et al., "Effects of Overexpression of Pancreatic Derived Factor (FAM3B) in Isolated Mouse Islets and Insulin-Secreting betaTC3 cells," Am. J. Physiol. Endocrinol. Metab. 289: E550 (2005).

Schulte, "The Use of Biomarks in Surveillance, Medical Screening, and Intervention," Mutat. Res. 592(1-2), pp. 155-163 (2005).

Kingsmore, "Multiplexed Protein Measurement: Technologies and Applications of Protein and Antibody Arrays," Nat. Rev. Drug. Discov., vol. 5, No. 4, pp. 310-320 (2006).

\* cited by examiner

MEANS AND METHODS FOR DIAGNOSING PANCREATIC CANCER

CROSS-REFERENCE TO RELATED APPLICATIONS

This application is a divisional of U.S. patent application Ser. No. 13/576,912, filed Oct. 4, 2012, which is the National Phase of International Patent Application No. PCT/EP2011/052182, filed Feb. 15, 2011, which claims priority from European Patent Application No. 10001596.5, filed Feb. 17, 2010. The contents of these applications are incorporated herein by reference in their entirety.

The present invention pertains to the field of cancer diagnosis. Specifically, it relates to a method for diagnosing pancreas cancer in a subject comprising the steps of determining in a sample of a subject suspected to suffer from pancreas cancer the amount of at least one biomarker selected from the biomarkers shown in Table 1 and comparing the said amount of the at least one biomarker with a reference, whereby pancreas cancer is to be diagnosed. The present invention also contemplates a method for identifying whether a subject is in need of a pancreas cancer therapy comprising the steps of the aforementioned methods and the further step of identifying a subject in need of a pancreas cancer therapy if said subject is to be diagnosed to suffer from pancreas cancer. Contemplated are, furthermore, diagnostic devices and kits for carrying out said methods.

Patients with carcinoma of the exocrine pancreas (adenocarcinoma) have a poor prognosis with a five-year survival rate of <5% and a median survival of 4-6 months (Jemal et al. 2009, CA Cancer J Clin 59(4): 225-249). Even after surgical intervention, the five-year survival rate is between 15% and 40% (Goggins 2005, J Clinical Oncology 23(20): 4524-4531). The nonspecific or apparently absent early clinical features make pancreatic cancer a silent and devastating cancer for which there is currently no screening method for early detection. Current methods for diagnosing pancreatic caner are rather ineffective at identifying smaller potentially curable lesions. Sensitive and specific biomarkers are needed to improve the early diagnosis.

At present, the carbohydrate antigen CA 19.9 is the only commercially available biomarker for pancreatic cancer. CA 19.9 is a tumor-associated antigen which has been originally isolated from a human colon cancer cell line. It is present on gangliosides in tissues and carried by glycoproteins in serum. The oligosaccharide which carries the CA 19.9 antigen is related to sialylated Lewis A blood group antigen. Lewis A antigen must be present before CA 19.9 can be expressed. CA 19.9 is synthesized by normal cells in pancreatic and bile ducts, gastric and colonic mucosa, bronchial and salivary glands, endometrium, and prostate.

However, the sensitivity of CA 19.9 in asymptomatic patients is low. Serum levels are elevated in less than 30% of patients with stage 1 cancers. Moreover, elevated CA 19.9 levels are not specific for pancreatic cancer but are elevated in other benign and malignant disorders.

Recent efforts focused on MIC-1 (macrophage inhibitory cytokine-1) as a serum biomarker. However, MIC-1 turned out to be comparable to CA19.9 with respect to sensitivity and specificity (Goggins, loc. cit.).

Genetic biomarkers such as mutations in K-ras and TP53 have been also identified as potential biomarkers for pancreatic cancer. However, the wide spread application of such biomarkers depends on the accuracy of the detection methods for the individual mutations which are rather inconvenient at present (Goggins, loc. cit.).

Therefore, there is still a need for a more reliable biomarker for diagnosing pancreatic cancer. In light of the severe consequences of the disease and the unspecific clinical symptoms at the beginning of the disease, such a biomarker could strengthen diagnostic and therapeutic approaches against pancreatic cancer.

Thus, the present invention relates to a method for diagnosing pancreas cancer in a subject comprising the steps of:
(a) determining in a sample of a subject suspected to suffer from pancreas cancer the amount of at least one biomarker selected from the biomarkers shown in Table 1; and
(b) comparing the said amount of the at least one biomarker with a reference, whereby pancreas cancer is to be diagnosed.

The term "diagnosing" as used herein means assessing whether a subject suffers from pancreatic cancer. As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention. Diagnosing according to the present invention includes applications of the method in monitoring, confirmation, and subclassification of the relevant disease or its symptoms.

The term "pancreatic cancer" as used herein refers to cancer which is derived from pancreatic cells. Preferably, pancreatic cancer as used herein is pancreatic adenocarcinoma. The symptoms and implications accompanying pancreatic cancer are well known from standard text books of medicine such as Stedmen or Pschyrembl.

The term "subject" as used herein relates to animals, preferably mammals, and, more preferably, humans. Preferably, the method of the present invention will be applied for subjects suspected to either suffer from pancreatic cancer in light of clinically apparent symptoms or subjects suspected to suffer from cancer due to a potential increased predisposition. The latter subjects may be subjects suffering from chronic pancreatitis, subjects with a familiar background (i.e. subjects from families where family members suffered already from pancreatic cancer) or subjects with genetic mutations influencing pancreatic cancer, e.g., Peutz-Jeghers syndrome.

The term "biomarker" as used herein refers to a polypeptide as shown in Table 1 or a fragment or variant of such a polypeptide being associated to the presence or absence of pancreatic cancer to the same extent as the well known polypeptides recited in Table 1. The polypeptide biomarkers listed in Table 1, preferably, encompass the polypeptides referred to by public Uni Prot Accession numbers as well as variants of said polypeptides having essentially the same immunological and/or biological properties. Variants include polypeptides differ in their amino acid sequence due to the presence of conservative amino acid substitutions. Preferably, such variants have an amino acid sequence being at least 70%, at least 80%, at least 90%, at least 95%, at least 98% or at least 99% identical to the amino acid sequences of the aforementioned specific polypeptides. Variants may be allelic variants, splice variants or any other species specific homologs, paralogs, or orthologs. Preferably, the percent identity can be determined by the algorithms of Needleman and Wunsch or Smith and Waterman. To carry out the sequence alignments, the program PileUp (J. Mol. Evolution., 25, 351-360, 1987 , Higgins et al., CABIOS, 5 1989: 151-153) or the programs Gap and BestFit (Needleman 1970, J. Mol. Biol. 48; 443-453 and Smith 1981, Adv. Appl. Math. 2; 482-489), which are part of the GCG software packet (Genetics Computer Group, 575 Science Drive, Madison, Wis., USA 53711, Version 1991), are preferably to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

In a preferred embodiment of the method of the present invention, said at least one biomarker is selected from the biomarkers shown in Tables 2a or 2b and wherein the subject is a female. In another preferred embodiment of the method of the present invention, said at least one biomarker is selected from the biomarkers shown in Tables 3a or 3b and wherein said subject is a male.

The term "sample" refers to a sample of a body fluid, to a sample of separated cells or to a sample from a tissue or an organ. Samples of body fluids can be obtained by well known techniques and include, preferably, samples of blood, plasma, serum, pancreatic juice, or more preferably, samples of urine. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

Determining the amount of the polypeptide biomarkers referred to in this specification relates to measuring the amount or concentration, preferably semi-quantitatively or quantitatively. Measuring can be done directly or indirectly. Direct measuring relates to measuring the amount or concentration of the polypeptide based on a signal which is obtained from the polypeptide itself and the intensity of which directly correlates with the number of molecules of the polypeptide present in the sample. Such a signal—sometimes referred to herein as intensity signal may be obtained, e.g., by measuring an intensity value of a specific physical or chemical property of the polypeptide. Indirect measuring includes measuring of a signal obtained from a secondary component (i.e. a component not being the polypeptide itself) or a biological read out system, e.g., measurable cellular responses, ligands, labels, or enzymatic reaction products.

In accordance with the present invention, determining the amount of a polypeptide biomarker can be achieved by all known means for determining the amount of a polypeptide in a sample.

Said means comprise immunoassay devices and methods which may utilize labeled molecules in various sandwich, competition, or other assay formats. Preferably, the immunoassay device is an antibody microarray. Said assays will develop a signal which is indicative for the presence or absence of the polypeptide and, thus, the biomarker.

Moreover, the signal strength can, preferably, be correlated directly or indirectly (e.g. reverse-proportional) to the amount of polypeptide present in a sample. Further suitable methods comprise measuring a physical or chemical property specific for the polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays, CBA (an enzymatic Cobalt Binding Assay), and latex agglutination assays.

Preferably, determining the amount of a polypeptide biomarker comprises the steps of (a) contacting a cell capable of eliciting a cellular response the intensity of which is indicative of the amount of the polypeptide with the said polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the polypeptide.

Also preferably, determining the amount of a polypeptide biomarker comprises the step of measuring a specific intensity signal obtainable from the polypeptide in the sample. As described above, such a signal may be the signal intensity observed at a mass to charge (m/z) variable specific for the polypeptide observed in mass spectra or a NMR spectrum specific for the polypeptide.

Determining the amount of a polypeptide biomarker may, preferably, comprise the steps of (a) contacting the polypeptide with a specific ligand, (b) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the polypeptide described herein. Preferred ligands include antibodies, nucleic acids, peptides or polypeptides such as receptors or binding partners for the polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab, scFv and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. Alternatively, chimeric mouse antibodies with rabbit Fc can be used.

The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the polypeptide. Specific binding according to the present invention means that the ligand or agent should not bind substantially to ("cross-react" with) another peptide, polypeptide or substance present in the sample to be analyzed. Preferably, the specifically bound polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semiquantitative or quantitative. Suitable methods are described in the following. First, binding of a ligand may be measured directly, e.g. by mass spectroscopy, NMR or surface plasmon resonance. Second, if the ligand also serves as a substrate of an enzymatic activity of the polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/polypeptide" complex or the ligand which was bound by the polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g. detectable) amount of product can be measured. Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethyl-benzidine, NBT-BCIP (4-nitro blue tetrazolium chloride and 5-bromo-4-chloro-3-indolyl-phosphate, available as ready-made stock solution from Roche Diagnostics), CDP-Star (™) (Amersham Biosciences), ECF(™) (Amersham Biosciences). A suitable enzyme-substrate combination may result in a colored reaction product, fluorescence or chemo luminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, or Dy-547, Dy-549, Dy-647, Dy-649 (Dyomics, Jena, Germany) or Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $<35>S$, $<125>I$, $<32>P$, $<33>P$ and the like. A radioactive label can be detected by any method known and appropriate, e.g. a light-sensitive film or a phosphor imager. Suitable measurement methods according the present invention also include precipitation (particularly immunoprecipitation), electro-chemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), FRET based proximity assays (Anal Chem. 2005 Apr 15;77(8): 2637-42.) or Ligation proximity assays (Nature Biotechnology 20, 473-477 (2002), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

The amount of a polypeptide biomarker may be, also preferably, determined as follows: (a) contacting a solid support comprising a ligand for the polypeptide as specified above with a sample comprising the polypeptide and (b) measuring the amount of polypeptide which is bound to the support. The ligand, preferably, chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known, see e.g., U.S. Pat. No. 5,744,305.

The term "amount" as used herein encompasses the absolute amount of a biomarker, the relative amount or concentration of the said biomarker as well as any value or parameter which correlates thereto or can be derived therefrom. Such values or parameters comprise intensity signal values from all specific physical or chemical properties obtained from the said biomarker by direct measurements, e.g., intensity values in mass spectra or NMR spectra or surface Plasmon resonance spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations. The term "comparing" as used herein encompasses comparing the amount of the biomarker comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amount determined in step a) and the reference amount, it is possible to diagnose pancreatic cancer.

Accordingly, the term "reference" as used herein refers to amounts of the biomarker which allow for determining whether a subject suffers from pancreatic cancer, or not. Therefore, the reference may either be derived from (i) a subject known to suffer from pancreatic cancer or (ii) a subject known not to suffer from pancreatic cancer, i.e. a healthy subject with respect to pancreatic cancer and, preferably, other diseases as well. Preferably, said reference is derived from a sample of a subject known not to suffer from cancer. More preferably, an increase in the amount of the said at least one biomarker selected from the biomarkers shown in Tables 2a or 3a compared to the reference is indicative for pancreas cancer whereas a decrease in the amount of the said at least one biomarker selected from the biomarkers shown in Tables 2b or 3b compared to the reference is indicative for pancreas cancer.

Moreover, the references, preferably, define threshold amounts or thresholds. Suitable reference amounts or threshold amounts may be determined by the method of the present invention from a reference sample to be analyzed together, i.e. simultaneously or subsequently, with the test sample. A preferred reference amount serving as a threshold may be derived from the upper limit of normal (ULN), i.e. the upper limit of the physiological amount to be found in a population of subjects (e.g. patients enrolled for a clinical trial). The ULN for a given population of subjects can be determined by various well known techniques. A suitable technique may be to determine the median of the population for the peptide or polypeptide amounts to be determined in the method of the present invention. Suitable threshold amounts can also be identified by ROC plots depicting the overlap between the two distributions by plotting the sensitivity versus 1-specificity for the complete range of decision thresholds. On the y-axis is sensitivity, or the true-positive fraction, defined as (number of true-positive test results)/(number of true-positive+number of false-negative test results). This has also been referred to as positivity in the presence of a given disease. It is calculated solely from the affected subgroup. On the x-axis is the false-positive fraction, or 1-specificity, defined as (number of false-positive results)/(number of true-negative+number of false-positive results). It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45 degrees diagonal line from the lower left corner to the upper right corner. Most plots fall in between these two extremes.

Advantageously, it has been found in the study underlying the present invention that the biomarkers listed in the tables are indicative for the presence or absence of a pancreatic cancer in a subject. Thereby, pancreatic cancer can be determined at early stages where the pancreatic cancer elicits rather unspecific clinical symptoms. As a consequence of the early diagnosis by the method of the present invention, therapeutic approaches can be applied earlier and may, therefore, allow for a more successful treatment of the disease by identifying subjects in need of a therapy at an early stage. Moreover, the findings underlying the aforementioned method also allow for an improved clinical management of pancreatic cancer since patients can be identified which need intensive monitoring. Further, the success of a therapy can be monitored. In the studies underlying this invention, urine samples from healthy patients and patients suffering from pancreatic cancer were analyzed using antibody microarrays comprising antibodies against 810 different polypeptides. Differences in the polypeptide amounts between healthy and diseased patients which turned out to be statistically significant are shown in the Tables below and could be used as biomarkers for diagnosing pancreatic cancer.

The present invention also relates to a method for identifying whether a subject is in need of a pancreas cancer therapy comprising the steps of the aforementioned methods and the further step of identifying a subject in need of a pancreas cancer therapy if said subject is to be diagnosed to suffer from pancreas cancer.

Preferably, the term " pancreas cancer therapy" comprises surgery, radiotherapy or drug treatment. Preferred therapies include resect neoplasm (for patients with sporadic disease, pancreaticoduodenectomy, tail pancreatectomy), pancreatectomy, adjuvant 5-FU based chemotherapy, adjuvant gemcitabine chemotherapy, doxorubicin (DOX), folinic acid (FA), or Mytomycin (MMC) adjuvant based chemotherapies, administration of one or more of the following drugs: 5-Fluorouracil (SFU, an inhibitor of thymidylate synthetase), Gemcitabine (nucleoside analogue), Capecitabine (Xeloda, a new oral, fluoropyrimidine carbamate that is sequentially converted to 5FU by three enzymes located in the liver and in tumours, including pancreatic cancer), Gemcitabine combined with Capecitabine, platinum-based agents, erlotinib (EGFR tyrosine kinase inhibitor , Trial: PA3 (Canada, USA)), cetuximab (monoclonal antibody to EGFR, Trial: SWOG S0205 (USA), bevacizumab (anti-VEGFR antibody (Avastin), Trial: CALGB 80303 (USA), Avita (Europe, Closed prematurely)), or GV1001 [+GMCSF] (peptide vaccine targeting telomerase (GV1001 (Europe, Australia) TeloVac (UK)). Radiotherapy has been widely used for the treatment of pancreatic cancer. The main drawback is the limit on the dosage owing to the close proximity of adjacent radiosensitive organs. External beam radiotherapy is routinely used with 5FU as a radiosensitising agent chemoradiotherapy), although gemcitabine is now being evaluated as an alternative radio-sensitiser. Newer techniques such as conformal radiotherapy are now being used, but these studies almost invariably employ follow-on chemotherapy once the chemoradiotherapy has been completed. A recent meta-analysis demonstrated that chemoradiotherapy is better than radiotherapy alone and that there is no survival difference between chemoradiotherapy plus follow-on chemotherapy and chemotherapy alone. A recent phase III study compared chemoradiotherapy and follow-on gemcitabine with gemcitabine alone in patients with locally advanced disease. The trial was closed prematurely because of significant toxicity in the combination arm and significantly reduced median survival in the combination arm (8.4 vs 14.3 months; p=0.014).

The phrase " a subject in need of a pancreas cancer therapy" as used herein relates to a subject which suffers from pancreatic cancer as diagnosed by the method of the present invention. It will be understood that a pancreas therapy is at least beneficial for such subjects being confirmed by the diagnostic method of the present invention. As discussed above, the diagnostic method of the present invention already allows identifying subjects at the early onset of the disease. Accordingly, such subjects which may not be unambiguously identifiable based on their clinical symptoms.

The present invention relates to a device for diagnosing pancreas cancer in a sample of a subject comprising:
  (a) an analyzing unit for the said sample of the subject comprising a detection agent for at least one biomarker as shown in any one of Tables 1, 2a, 2b, 3a or 3b, said detection agent allowing for the determination of the amount of the said at least one biomarker in the sample; and operatively linked thereto,
  (b) an evaluation unit comprising a data processing unit and a data base, said data base comprising a stored reference and said data processing unit being capable of carrying out a comparison of the amount of the at least one biomarker determined by the analyzing unit and the stored reference thereby establishing the diagnosis.

The term "device" as used herein relates to a system of means comprising at least the aforementioned analyzing unit and the evaluation unit operatively linked to each other as to allow the diagnosis. Preferred detection agents to be used for the device of the present invention are disclosed above in connection with the method of the invention. Preferably, detection agents are antibodies or aptameres. How to link the units of the device in an operating manner will depend on the type of units included into the device. For example, where units for automatically determining the amount of the biomarker are applied, the data obtained by said automatically operating unit can be processed by, e.g., a computer program in order to obtain the desired results. Preferably, the units are comprised by a single device in such a case. The computer unit, preferably, comprises a database including the stored reference(s) as well as a computer-implemented algorithm for carrying out a comparison of the determined amounts for the polypeptide biomarkers with the stored reference of the database. Computer-implemented as used herein refers to a computer-readable program code tangibly included into the computer unit. The results may be given as output of raw data which need interpretation by the clinician. Preferably, the output of the device is, however, processed, i.e. evaluated, raw data the interpretation of which does not require a clinician.

In a preferred device of the invention, the detection agent, preferably, an antibody, is immobilized on a solid support in an array format. It will be understood that a device according to the present invention can determine the amount of more than one biomarker simultaneously. To this end, the detection agents may be immobilized on a solid support and arranged in an array format, e.g., in a so called " microarray".

The present invention also relates to a kit comprising a detection agent for determining the amount of at least one biomarker as shown in any one of Tables 1, 2a, 2b, 3a or 3b and a evaluation instructions for establishing the diagnosis.

The term "kit" as used herein refers to a collection of the aforementioned agent and the instructions provided in a ready-to-use manner for determining the biomarker amount in a sample. The agent and the instructions are, preferably, provided in a single container.

Preferably, the kit also comprises further components which are necessary for carrying out the determination of the amount of the biomarker. Such components may be auxiliary agents which are required for the detection of the biomarker or calibration standards. Moreover, the kit may, preferably, comprise agents for the detection of more than one biomarker.

In principle, the present invention contemplates the use of at least one biomarker as shown in any one of Tables 1, 2a, 2b, 3a or 3b, a detection agent therefore, the aforementioned devices or the aforementioned kits for diagnosing in a sample of a subject pancreas cancer.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

EXAMPLE

Identification of Polypeptide Biomarkers for Pancreas Cancer

In order to identify polypeptides with differential abundance in patients suffering from pancreatic cancer a study was performed utilising antibody microarrays. In antibody microarrays antibodies are immobilised at distinct locations on a solid support. After array printing with microarraying robots, the microarrays are blocked in order to minimize unspecific protein adsorption on the array surface. The arrays are then incubated with the protein samples of interest. In this study the protein fraction of the samples was directly labeled by a fluorescent dye, using NHS-ester chemistry.

For inclusion on the array specific target proteins were selected by transcriptional studies on pancreatic cancer and other cancer entities. The antibody microarray applied in this study comprised 810 antibodies that were directed at 741 different proteins. All antibodies were immobilised in duplicates. The study involved twelve urine samples from six patients with pancreatic adenocarcinoma and six healthy individuals, both groups equally divided into male and female.

For the analyses from the 12 individuals midstream urine samples were collected and pH was adjusted to 7. The samples were desalted and concentrated as described in detail elsewhere (Weeks et al. (2008) Proteomics: Clin. Appl. 2,1047-57). Briefly, samples were desalted using Zeba spin columns (Thermo Scientific). The flow-through was frozen in liquid nitrogen and lyophilised to dryness using an ILMVAC Freeze Dryer. Lyophilised samples were resolubilised in distilled water and concentrated with Vivaspin 15R-5 kDa (Sartorius Vivascience, Hannover, Germany).

The protein samples were labeled with Dy-549 (Dyomics, Jena, Germany). Additionally, a common reference was prepared by pooling of samples and subsequent labeling with Dy649 (Dyomics, Jena, Germany). All protein samples were labeled at a protein concentration of 4 mg/m with 0.4 mg/mL of the NHS-esters of the fluorescent dyes in 100 mM sodium bicarbonate buffer (pH 9.0), 1% (w/v) Triton-100 on a shaker at 4° C. After 1 h, the reactions were stopped by addition of hydroxylamine to 1 M. Unreacted dye was removed 30 min later and the buffer changed to PBS using Zeba Desalt columns (Thermo Scientific). Subsequently, Complete Protease Inhibitor Cocktail tablets (Roche, Mannheim, Germany) were added as recommended by the manufacturer.

Incubations were performed in homemade incubation chambers, which were attached to the array slides with Terostat-81 (Henkel, Dusseldorf, Germany). The inner dimensions of the incubation chambers matched the area of the array (9 mm×18 mm) with an additional border of 2 mm and a height of 5 mm. Prior to adding the labeled protein samples, the arrays were blocked in a casein-based blocking solution (Candor Biosciences, Weißensberg, Germany) on a Slidebooster instrument (Advalytix, Munich, Germany) for 3 h. Incubation was performed with labeled samples diluted 1:20 in blocking solution containing 1% (w/v) Tween-20 and Complete Protease Inhibitor Cocktail for 15 h in a total volume of 600 µl. All samples were incubated in a dual-colour assay. In this assay each sample is incubated in combination with the common reference labeled with a different dye. After incubation, slides were thoroughly washed with PBSTT prior and after detaching the incubation chambers. Finally, the slides were rinsed with 0.1×PBS and distilled water and dried in a stream of air.

Slide scanning was done on a ScanArray 5000 or 4000 XL unit (Packard, Billerica, USA) using the identical instrument laser power and PMT in each experiment. Spot segmentation was performed with GenePix Pro 6.0 (Molecular Devices, Union City, USA). Resulting data were analyzed using the LIMMA package of R-Bioconductor after uploading the mean signal and median background intensities. The intensity values were background-corrected using the Normexp method with an offset of 50. The log-ratios of the two colour channels were normalized with global Lowess. For differential analyses of the depletion experiment a two-factorial linear model (gender and cancer) was fitted using LIMMA resulting in a F-test based on moderated statistics. All p-values were adjusted for multiple testing by controlling the false discovery rate according to Benjamini and Hochberg.

Using LIMMA analysis, 11 proteins were found at differential levels between healthy males and females at a significance level of adj. P<0.05 with the most prominent one being KLK3 (also known as PSA; p=1·10−5). Proteins with different abundances in patients and controls differed highly in female and male. Therefore, separated gender specific comparisons were performed. We found two proteins that differ between healthy and diseased females, whereas 17 proteins showed significantly differential levels within the male subgroup. The respective log-fold changes between cancerous samples and healthy controls are summarised in the tables below.

For validation, a classification test (prediction analyses for microarrays/PAM) was performed using the pamr-package for the statistical system R. For this the samples were grouped according health status and gender. In an inner loop a classificator was optimised by leave-one-out procedure. In an outer loop the accuracy of the respective classificator was estimated by a leave-one-out cross validation. Even within this small sample set an overall accuracy of 72% was obtained. Pancreatic cancer could be detected with a sensitivity and a specificity of 83%.

The results of the aforementioned study are summarized in the following Tables:

TABLE 1

| Nr | Protein Short | Log-FC | adj. P. Val | HGNC-Symbol | Uniprot Accession | Protein name | Official gene name |
|---|---|---|---|---|---|---|---|
| 1 | TMM54 | −1.0 | 4.97E−02 | TMEM54 | Q969K7 | Transmembrane protein 54 | transmembrane protein 54 |
| 2 | MK12 | −0.8 | 2.99E−02 | MAPK12 | P53778 | Mitogen-activated protein kinase 12 | mitogen-activated protein kinase 12 |
| 3 | MELPH | −1.0 | 4.37E−02 | MLPH | Q9BV36 | Melanophilin | melanophilin |
| 4 | UN93B | −0.8 | 3.12E−02 | UNC93B1 | Q9H1C4 | Protein unc-93 homolog B1 | unc-93 homolog B1 (C. elegans) |
| 5 | COXAM | −0.8 | 4.83E−02 | CMC1 | Q7Z7K0 | COX assembly mitochondrial protein homolog | COX assembly mitochondrial protein homolog (S. cerevisiae) |
| 6 | RASF1 | 1.2 | 9.75E−02 | RASSF1 | Q9NS23 | Ras association domain-containing protein 1 | Ras association (RalGDS/AF-6) domain family member 1 |
| 7 | AKTIP | −1.0 | 5.92E−02 | AKTIP | Q9H8T0 | AKT-interacting protein | AKT interacting protein |
| 8 | CASPA | −2.0 | 5.86E−02 | CASP10 | Q92851 | Caspase-10 subunit p23/17 | caspase 10, apoptosis-related cysteine peptidase |

TABLE 1-continued

| Nr | Protein Short | Log-FC | adj. P. Val | HGNC-Symbol | Uniprot Accession | Protein name | Official gene name |
|---|---|---|---|---|---|---|---|
| 9 | CDN2B | −1.6 | 7.04E−02 | CDKN2B | P42772 | Cyclin-dependent kinase 4 inhibitor B | cyclin-dependent kinase inhibitor 2B (p15, inhibits CDK4) |
| 10 | CLD7 | −0.9 | 5.86E−02 | CLDN7 | O95471 | Claudin-7 | claudin 7 |
| 11 | DCOR | 0.5 | 8.81E−02 | ODC1 | P11926 | Ornithine decarboxylase | ornithine decarboxylase 1 |
| 12 | EWS | −0.5 | 9.75E−02 | EWSR1 | Q01844 | RNA-binding protein EWS | Ewing sarcoma breakpoint region 1 |
| 13 | FAK1 | −0.7 | 4.83E−02 | PTK2 | Q05397 | Focal adhesion kinase 1 | PTK2 protein tyrosine kinase 2 |
| 14 | GPX4 | 0.4 | 9.75E−02 | GPX4 | P36969 | Phospholipid hydroperoxide glutathione peroxidase, mitochondrial | glutathione peroxidase 4 (phospholipid hydroperoxidase) |
| 15 | HMGB2 | 0.5 | 5.15E−02 | HMGB2 | P26583 | High mobility group protein B2 | high-mobility group box 2 |
| 16 | IGF1A | −1.2 | 4.97E−02 | IGF1 | P01343 | Insulin-like growth factor IA | insulin-like growth factor 1 (somatomedin C) |
| 17 | IRS2 | −0.7 | 5.92E−02 | IRS2 | Q9Y4H2 | Insulin receptor substrate 2 | insulin receptor substrate 2 |
| 18 | K2C8 | −0.8 | 4.37E−02 | KRT8 | P05787 | Keratin, type II cytoskeletal 8 | keratin 8 |
| 19 | LYAM1 | −0.9 | 5.86E−02 | SELL | P14151 | L-selectin | selectin L |
| 20 | MAD4 | −0.9 | 8.22E−02 | MXD4 | Q14582 | Max-interacting transcriptional repressor MAD4 | MAX dimerization protein 4 |
| 21 | MMP1 | −0.8 | 8.56E−02 | MMP1 | P03956 | 27 kDa interstitial collagenase | matrix metallopeptidase 1 (interstitial collagenase) |
| 22 | MMP7 | −0.8 | 9.75E−02 | MMP7 | P09237 | Matrilysin | matrix metallopeptidase 7 (matrilysin, uterine) |
| 23 | MUC5B | 0.6 | 4.83E−02 | MUC5B | Q9HC84 | Mucin-5B | mucin 5B, oligomeric mucus/gel-forming |
| 24 | S10A6 | −2.4 | 5.92E−02 | S100A6 | P06703 | Protein S100-A6 | S100 calcium binding protein A6 |
| 25 | SORL | −0.9 | 5.96E−02 | SORL1 | Q92673 | Sortilin-related receptor | sortilin-related receptor, L(DLR class) A repeats-containing |
| 26 | TNR6 | −1.6 | 4.41E−02 | FAS | P25445 | Tumor necrosis factor receptor superfamily member 6 | Fas (TNF receptor superfamily, member 6) |
| 27 | WDR1 | −0.7 | 5.86E−02 | WDR1 | O75083 | WD repeat-containing protein 1 | WD repeat domain 1 |

TABLE 2a

| Nr | Protein Short | Log-FC | adj. P. Val | HGNC-Symbol | Uniprot Accession | Protein name | Official gene name |
|---|---|---|---|---|---|---|---|
| 1 | DCOR | 0.5 | 8.81E−02 | ODC1 | P11926 | Ornithine decarboxylase | ornithine decarboxylase 1 |

TABLE 2b

| Nr | Protein Short | Log-FC | adj. P. Val | HGNC-Symbol | Uniprot Accession | Protein name | Official gene name |
|---|---|---|---|---|---|---|---|
| 1 | AKTIP | −1.0 | 5.92E−02 | AKTIP | Q9H8T0 | AKT-interacting protein | AKT interacting protein |
| 2 | CASPA | −2.0 | 5.86E−02 | CASP10 | Q92851 | Caspase-10 subunit p23/17 | caspase 10, apoptosis-related cysteine peptidase |
| 3 | CDN2B | −1.6 | 7.04E−02 | CDKN2B | P42772 | Cyclin-dependent kinase 4 inhibitor B | cyclin-dependent kinase inhibitor 2B (p15, inhibits CDK4) |
| 4 | CLD7 | −0.9 | 5.86E−02 | CLDN7 | O95471 | Claudin-7 | claudin 7 |
| 5 | IRS2 | −0.7 | 5.92E−02 | IRS2 | Q9Y4H2 | Insulin receptor substrate 2 | insulin receptor substrate 2 |
| 6 | LYAM1 | −0.9 | 5.86E−02 | SELL | P14151 | L-selectin | selectin L |
| 7 | SORL | −0.9 | 5.96E−02 | SORL1 | Q92673 | Sortilin-related receptor | sortilin-related receptor, L(DLR class) A repeats-containing |
| 8 | WDR1 | −0.7 | 5.86E−02 | WDR1 | O75083 | WD repeat-containing protein 1 | WD repeat domain 1 |

TABLE 3a

| Nr | Protein Short | Log-FC | adj. P. Val | HGNC-Symbol | Uniprot Accession | Protein name | Official gene name |
|---|---|---|---|---|---|---|---|
| 1 | GPX4 | 0.4 | 9.75E−02 | GPX4 | P36969 | Phospholipid hydroperoxide glutathione peroxidase, mitochondrial | glutathione peroxidase 4 (phospholipid hydroperoxidase) |

TABLE 3a-continued

| Nr | Protein Short | Log-FC | adj. P. Val | HGNC-Symbol | Uniprot Accession | Protein name | Official gene name |
|----|---------------|--------|-------------|-------------|-------------------|--------------|--------------------|
| 2 | HMGB2 | 0.5 | 5.15E-02 | HMGB2 | P26583 | High mobility group protein B2 | high-mobility group box 2 |
| 3 | MUC5B | 0.6 | 4.83E-02 | MUC5B | Q9HC84 | Mucin-5B | mucin 5B, oligomeric mucus/gel-forming |
| 4 | RASF1 | 1.2 | 9.75E-02 | RASSF1 | Q9NS23 | Ras association domain-containing protein 1 | Ras association (RalGDS/AF-6) domain family member 1 |

TABLE 3b

| Nr | Protein Short | Log-FC | adj. P. Val | HGNC-Symbol | Uniprot Accession | Protein name | Official gene name |
|----|---------------|--------|-------------|-------------|-------------------|--------------|--------------------|
| 1 | COXAM | -0.8 | 4.83E-02 | CMC1 | Q7Z7K0 | COX assembly mitochondrial protein homolog | COX assembly mitochondrial protein homolog (*S. cerevisiae*) |
| 2 | EWS | -0.5 | 9.75E-02 | EWSR1 | Q01844 | RNA-binding protein EWS | Ewing sarcoma breakpoint region 1 |
| 3 | FAK1 | -0.7 | 4.83E-02 | PTK2 | Q05397 | Focal adhesion kinase 1 | PTK2 protein tyrosine kinase 2 |
| 4 | IGF1A | -1.2 | 4.97E-02 | IGF1 | P01343 | Insulin-like growth factor IA | insulin-like growth factor 1 (somatomedin C) |
| 5 | K2C8 | -0.8 | 4.37E-02 | KRT8 | P05787 | Keratin, type II cytoskeletal 8 | keratin 8 |
| 6 | MAD4 | -0.9 | 8.22E-02 | MXD4 | Q14582 | Max-interacting transcriptional repressor MAD4 | MAX dimerization protein 4 |
| 7 | MELPH | -1.0 | 4.37E-02 | MLPH | Q9BV36 | Melanophilin | melanophilin |
| 8 | MK12 | -0.8 | 2.99E-02 | MAPK12 | P53778 | Mitogen-activated protein kinase 12 | mitogen-activated protein kinase 12 |
| 9 | MMP1 | -0.8 | 8.56E-02 | MMP1 | P03956 | 27 kDa interstitial collagenase | matrix metallopeptidase 1 (interstitial collagenase) |
| 10 | MMP7 | -0.8 | 9.75E-02 | MMP7 | P09237 | Matrilysin | matrix metallopeptidase 7 (matrilysin, uterine) |
| 11 | S10A6 | -2.4 | 5.92E-02 | S100A6 | P06703 | Protein S100-A6 | S100 calcium binding protein A6 |
| 12 | TMM54 | -1.0 | 4.97E-02 | TMEM54 | Q969K7 | Transmembrane protein 54 | transmembrane protein 54 |
| 13 | TNR6 | -1.6 | 4.41E-02 | FAS | P25445 | Tumor necrosis factor receptor superfamily member 6 | Fas (TNF receptor superfamily, member 6) |
| 14 | UN93B | -0.8 | 3.12E-02 | UNC93B1 | Q9H1C4 | Protein unc-93 homolog B1 | unc-93 homolog B1 (*C. elegans*) |

The invention claimed is:

1. A method of treating pancreatic cancer in a subject comprising the steps of:
   (a) determining in a sample of a subject suspected to suffer from pancreas cancer the amount of at least three polypeptide biomarkers selected from TMM54, MK12, MELPH, UN93B, COXAM, RASF1, AKTIP, CASPA, CDN2B, CLD7, DCOR, EWS, FAK1, GPX4, HMGB2, IGF1A, IRS2, K2C8, LYAM1, MAD4, MMP1, MMP7, S10A6, SORL, and TNR6, wherein the sample is a blood, plasma, serum, or urine sample, wherein the amount is determined with an immunoassay, wherein the immunoassay comprises:
      (i) contacting the sample with an antibody microarray comprising antibodies that recognize the at least three polypeptide biomarkers, and
      (ii) measuring the amounts of bound biomarkers and thereby determining the amounts of the biomarkers present in the sample;
   (b) comparing the amount of the at least three biomarkers with a reference to determine if the subject suffers from pancreas cancer, wherein a decrease in the amount of AKTIP, CASPA, CDN2B, CLD7, IRS2, LYAM1, SORL, COXAM, EWS, FAK1, IGF1A, K2C8, MAD4, MELPH, MK12, MMP1, MMP7, S10A6, TMM54, TNR6, and UN93B compared to the reference is indicative of pancreatic cancer, and/or an increase in the amount of DCOR, GPX4, HMGB2, or RASF1 as compared to the reference is indicative of pancreatic cancer; and
   (c) treating the subject with a pancreas cancer therapy if the subject is determined to suffer from pancreas cancer.

2. The method of claim 1, wherein said at least three polypeptide biomarkers are selected from DCOR, AKTIP, CASPA, CDN2B, CLD7, IRS2, LYAM1, SORL, and wherein the subject is a female.

3. The method of claim 1, wherein said at least three polypeptide biomarkers are selected from GPX4, HMGB2, RASF1, COXAM, EWS, FAK1, IGF1A, K2C8, MAD4, MELPH, MK12, MMP1, MMP7, S10A6, TMM54, TNR6, and UN93B, and wherein said subject is a male.

4. The method of claim 1, wherein said reference is derived from a sample of a subject known not to suffer from cancer.

5. The method of claim 1, wherein said pancreas cancer therapy comprises surgery, radiotherapy or drug treatment.

6. The method of claim 1, wherein said sample is a urine sample.

7. The method of claim 1, wherein said subject is a human.

8. The method of claim 1, wherein said subject is suspected to suffer from pancreas adenocarcinoma.

9. A method for treating pancreas cancer in a subject comprising the steps of:
   (a) determining or having determined in a sample from a subject suspected to suffer from pancreas cancer the amount of at least one polypeptide biomarker selected from TMM54, MK12, MELPH, UN93B, COXAM, RASF1, AKTIP, CASPA, CDN2B, CLD7, DCOR, EWS, FAK1, GPX4, IGF1A, IRS2, K2C8, LYAM1, MAD4, MMP7, S10A6, SORL, and WDR1, wherein the sample is a blood, plasma, serum, or urine sample; and
   (b) comparing or having compared the amount of the at least one biomarker with a reference, whereby pancreas cancer is to be diagnosed, wherein an increase in the amount of DCOR, GPX4, or RASF1 as compared to the reference is indicative of pancreas cancer, and/or a decrease in the amount of AKTIP, CASPA, CDN2B, CLD7, IRS2, LYAM1, SORL, WDR1, COXAM, EWS, FAK1, IGF1A, K2C8, MAD4, MELPH, MK12, MMP7, S10A6, TMM54, and UN93B compared to the reference is indicative of pancreas cancer; and
   (c) treating the subject with a pancreas cancer therapy if the subject is determined to suffer from pancreas cancer.

10. The method of claim 9, wherein the at least one polypeptide biomarker is selected from DCOR, AKTIP, CASPA, CDN2B, CLD7, IRS2, LYAM1, SORL, or WDR1 and wherein the subject is a female.

11. The method of claim 9, wherein the at least one polypeptide biomarker is selected from GPX4, RASF1, COXAM, EWS, FAK1, IGF1A, K2C8, MAD4, MELPH, MK12, MMP7, S10A6, TMM54, and UN93B, and wherein the subject is a male.

12. The method of claim 9, wherein the reference is derived from a sample of a subject known not to suffer from cancer.

13. The method of claim 9, wherein the pancreas cancer therapy comprises surgery, radiotherapy or drug treatment.

14. The method of claim 9, wherein the sample is a urine sample.

15. The method of claim 9, wherein the subject is a human.

16. The method of claim 9, wherein the pancreas cancer is pancreas adenocarcinoma.

* * * * *

SEQUENCE LISTING

<160> NUMBER OF SEQ ID NOS: 27

<210> SEQ ID NO 1
<211> LENGTH: 292
<212> TYPE: PRT
<213> ORGANISM: Homo sapiens

<400> SEQUENCE: 1

```
Met Asn Pro Phe Trp Ser Met Ser Thr Ser Ser Val Arg Lys Arg Ser
1               5                   10                  15

Glu Gly Glu Glu Lys Thr Leu Thr Gly Asp Val Lys Thr Ser Pro Pro
            20                  25                  30

Arg Thr Ala Pro Lys Lys Gln Leu Pro Ser Ile Pro Lys Asn Ala Leu
        35                  40                  45

Pro Ile Thr Lys Pro Thr Ser Pro Ala Pro Ala Ala Gln Ser Thr Asn
    50                  55                  60

Gly Thr His Ala Ser Tyr Gly Pro Phe Tyr Leu Glu Tyr Ser Leu Leu
65                  70                  75                  80

Ala Glu Phe Thr Leu Val Val Lys Gln Lys Leu Pro Gly Val Tyr Val
                85                  90                  95

Gln Pro Ser Tyr Arg Ser Ala Leu Met Trp Phe Gly Val Ile Phe Ile
            100                 105                 110

Arg His Gly Leu Tyr Gln Asp Gly Val Phe Lys Phe Thr Val Tyr Ile
        115                 120                 125
```

-continued

```
Pro Asp Asn Tyr Pro Asp Gly Asp Cys Pro Arg Leu Val Phe Asp Ile
130                 135                 140

Pro Val Phe His Pro Leu Val Asp Pro Thr Ser Gly Glu Leu Asp Val
145                 150                 155                 160

Lys Arg Ala Phe Ala Lys Trp Arg Arg Asn His Asn His Ile Trp Gln
                165                 170                 175

Val Leu Met Tyr Ala Arg Arg Val Phe Tyr Lys Ile Asp Thr Ala Ser
            180                 185                 190

Pro Leu Asn Pro Glu Ala Ala Val Leu Tyr Glu Lys Asp Ile Gln Leu
        195                 200                 205

Phe Lys Ser Lys Val Val Asp Ser Val Lys Val Cys Thr Ala Arg Leu
210                 215                 220

Phe Asp Gln Pro Lys Ile Glu Asp Pro Tyr Ala Ile Ser Phe Ser Pro
225                 230                 235                 240

Trp Asn Pro Ser Val His Asp Glu Ala Arg Glu Lys Met Leu Thr Gln
                245                 250                 255

Lys Lys Pro Glu Glu Gln His Asn Lys Ser Val His Val Ala Gly Leu
                260                 265                 270

Ser Trp Val Lys Pro Gly Ser Val Gln Pro Phe Ser Lys Glu Glu Lys
        275                 280                 285

Thr Val Ala Thr
        290

<210> SEQ ID NO 2
<211> LENGTH: 521
<212> TYPE: PRT
<213> ORGANISM: Homo sapiens

<400> SEQUENCE: 2

Met Lys Ser Gln Gly Gln His Trp Tyr Ser Ser Asp Lys Asn Cys
1               5                   10                  15

Lys Val Ser Phe Arg Glu Lys Leu Leu Ile Ile Asp Ser Asn Leu Gly
                20                  25                  30

Val Gln Asp Val Glu Asn Leu Lys Phe Leu Cys Ile Gly Leu Val Pro
            35                  40                  45

Asn Lys Lys Leu Glu Lys Ser Ser Ala Ser Asp Val Phe Glu His
        50                  55                  60

Leu Leu Ala Glu Asp Leu Leu Ser Glu Glu Asp Pro Phe Phe Leu Ala
65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
                100                 105                 110

Ser Leu Phe Arg Asn Leu Leu Tyr Glu Leu Ser Glu Gly Ile Asp Ser
            115                 120                 125

Glu Asn Leu Lys Asp Met Ile Phe Leu Leu Lys Asp Ser Leu Pro Lys
        130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205
```

Gln Gly Glu Glu Glu Leu Val Ser Gln Thr Asp Val Lys Thr Phe Leu
    210                 215                 220

Glu Ala Leu Pro Gln Glu Ser Trp Gln Asn Lys His Ala Gly Ser Asn
225                 230                 235                 240

Gly Asn Arg Ala Thr Asn Gly Ala Pro Ser Leu Val Ser Arg Gly Met
                245                 250                 255

Gln Gly Ala Ser Ala Asn Thr Leu Asn Ser Glu Thr Ser Thr Lys Arg
            260                 265                 270

Ala Ala Val Tyr Arg Met Asn Arg Asn His Arg Gly Leu Cys Val Ile
        275                 280                 285

Val Asn Asn His Ser Phe Thr Ser Leu Lys Asp Arg Gln Gly Thr His
    290                 295                 300

Lys Asp Ala Glu Ile Leu Ser His Val Phe Gln Trp Leu Gly Phe Thr
305                 310                 315                 320

Val His Ile His Asn Asn Val Thr Lys Val Glu Met Glu Met Val Leu
                325                 330                 335

Gln Lys Gln Lys Cys Asn Pro Ala His Ala Asp Gly Asp Cys Phe Val
            340                 345                 350

Phe Cys Ile Leu Thr His Gly Arg Phe Gly Ala Val Tyr Ser Ser Asp
        355                 360                 365

Glu Ala Leu Ile Pro Ile Arg Glu Ile Met Ser His Phe Thr Ala Leu
    370                 375                 380

Gln Cys Pro Arg Leu Ala Glu Lys Pro Lys Leu Phe Phe Ile Gln Ala
385                 390                 395                 400

Cys Gln Gly Glu Glu Ile Gln Pro Ser Val Ser Ile Glu Ala Asp Ala
                405                 410                 415

Leu Asn Pro Glu Gln Ala Pro Thr Ser Leu Gln Asp Ser Ile Pro Ala
            420                 425                 430

Glu Ala Asp Phe Leu Leu Gly Leu Ala Thr Val Pro Gly Tyr Val Ser
        435                 440                 445

Phe Arg His Val Glu Glu Gly Ser Trp Tyr Ile Gln Ser Leu Cys Asn
    450                 455                 460

His Leu Lys Lys Leu Val Pro Arg Met Leu Lys Phe Leu Glu Lys Thr
465                 470                 475                 480

Met Glu Ile Arg Gly Arg Lys Arg Thr Val Trp Gly Ala Lys Gln Ile
                485                 490                 495

Ser Ala Thr Ser Leu Pro Thr Ala Ile Ser Ala Gln Thr Pro Arg Pro
            500                 505                 510

Pro Met Arg Arg Trp Ser Ser Val Ser
        515                 520

<210> SEQ ID NO 3
<211> LENGTH: 138
<212> TYPE: PRT
<213> ORGANISM: Homo sapiens

<400> SEQUENCE: 3

Met Arg Glu Glu Asn Lys Gly Met Pro Ser Gly Gly Gly Ser Asp Glu
1               5                   10                  15

Gly Leu Ala Ser Ala Ala Ala Arg Gly Leu Val Glu Lys Val Arg Gln
            20                  25                  30

Leu Leu Glu Ala Gly Ala Asp Pro Asn Gly Val Asn Arg Phe Gly Arg
        35                  40                  45

Arg Ala Ile Gln Val Met Met Met Gly Ser Ala Arg Val Ala Glu Leu

```
                 50                  55                  60
Leu Leu Leu His Gly Ala Glu Pro Asn Cys Ala Asp Pro Ala Thr Leu
 65                  70                  75                  80

Thr Arg Pro Val His Asp Ala Ala Arg Glu Gly Phe Leu Asp Thr Leu
                 85                  90                  95

Val Val Leu His Arg Ala Gly Ala Arg Leu Asp Val Arg Asp Ala Trp
                100                 105                 110

Gly Arg Leu Pro Val Asp Leu Ala Glu Glu Arg Gly His Arg Asp Val
                115                 120                 125

Ala Gly Tyr Leu Arg Thr Ala Thr Gly Asp
                130                 135

<210> SEQ ID NO 4
<211> LENGTH: 211
<212> TYPE: PRT
<213> ORGANISM: Homo sapiens

<400> SEQUENCE: 4

Met Ala Asn Ser Gly Leu Gln Leu Leu Gly Phe Ser Met Ala Leu Leu
 1               5                  10                  15

Gly Trp Val Gly Leu Val Ala Cys Thr Ala Ile Pro Gln Trp Gln Met
                 20                  25                  30

Ser Ser Tyr Ala Gly Asp Asn Ile Ile Thr Ala Gln Ala Met Tyr Lys
                 35                  40                  45

Gly Leu Trp Met Asp Cys Val Thr Gln Ser Thr Gly Met Met Ser Cys
                 50                  55                  60

Lys Met Tyr Asp Ser Val Leu Ala Leu Ser Ala Ala Leu Gln Ala Thr
 65                  70                  75                  80

Arg Ala Leu Met Val Val Ser Leu Val Leu Gly Phe Leu Ala Met Phe
                 85                  90                  95

Val Ala Thr Met Gly Met Lys Cys Thr Arg Cys Gly Gly Asp Asp Lys
                100                 105                 110

Val Lys Lys Ala Arg Ile Ala Met Gly Gly Gly Ile Ile Phe Ile Val
                115                 120                 125

Ala Gly Leu Ala Ala Leu Val Ala Cys Ser Trp Tyr Gly His Gln Ile
                130                 135                 140

Val Thr Asp Phe Tyr Asn Pro Leu Ile Pro Thr Asn Ile Lys Tyr Glu
145                 150                 155                 160

Phe Gly Pro Ala Ile Phe Ile Gly Trp Ala Gly Ser Ala Leu Val Ile
                165                 170                 175

Leu Gly Gly Ala Leu Leu Ser Cys Ser Cys Pro Gly Asn Glu Ser Lys
                180                 185                 190

Ala Gly Tyr Arg Ala Pro Arg Ser Tyr Pro Lys Ser Asn Ser Ser Lys
                195                 200                 205

Glu Tyr Val
    210

<210> SEQ ID NO 5
<211> LENGTH: 106
<212> TYPE: PRT
<213> ORGANISM: Homo sapiens

<400> SEQUENCE: 5

Met Ala Leu Asp Pro Ala Asp Gln His Leu Arg His Val Glu Lys Asp
 1               5                  10                  15

Val Leu Ile Pro Lys Ile Met Arg Glu Lys Ala Lys Glu Arg Cys Ser
```

```
            20                  25                  30
Glu Gln Val Gln Asp Phe Thr Lys Cys Cys Lys Asn Ser Gly Val Leu
                35                  40                  45

Met Val Val Lys Cys Arg Lys Glu Asn Ser Ala Leu Lys Glu Cys Leu
 50                  55                  60

Thr Ala Tyr Tyr Asn Asp Pro Ala Phe Tyr Glu Cys Lys Met Glu
 65                  70                  75                  80

Tyr Leu Lys Glu Arg Glu Glu Phe Arg Lys Thr Gly Ile Pro Thr Lys
                85                  90                  95

Lys Arg Leu Gln Lys Leu Pro Thr Ser Met
                100                 105

<210> SEQ ID NO 6
<211> LENGTH: 461
<212> TYPE: PRT
<213> ORGANISM: Homo sapiens

<400> SEQUENCE: 6

Met Asn Asn Phe Gly Asn Glu Glu Phe Asp Cys His Phe Leu Asp Glu
 1               5                  10                  15

Gly Phe Thr Ala Lys Asp Ile Leu Asp Gln Lys Ile Asn Glu Val Ser
                20                  25                  30

Ser Ser Asp Asp Lys Asp Ala Phe Tyr Val Ala Asp Leu Gly Asp Ile
                35                  40                  45

Leu Lys Lys His Leu Arg Trp Leu Lys Ala Leu Pro Arg Val Thr Pro
 50                  55                  60

Phe Tyr Ala Val Lys Cys Asn Asp Ser Lys Ala Ile Val Lys Thr Leu
 65                  70                  75                  80

Ala Ala Thr Gly Thr Gly Phe Asp Cys Ala Ser Lys Thr Glu Ile Gln
                85                  90                  95

Leu Val Gln Ser Leu Gly Val Pro Pro Glu Arg Ile Ile Tyr Ala Asn
                100                 105                 110

Pro Cys Lys Gln Val Ser Gln Ile Lys Tyr Ala Ala Asn Asn Gly Val
                115                 120                 125

Gln Met Met Thr Phe Asp Ser Glu Val Glu Leu Met Lys Val Ala Arg
                130                 135                 140

Ala His Pro Lys Ala Lys Leu Val Leu Arg Ile Ala Thr Asp Asp Ser
145                 150                 155                 160

Lys Ala Val Cys Arg Leu Ser Val Lys Phe Gly Ala Thr Leu Arg Thr
                165                 170                 175

Ser Arg Leu Leu Leu Glu Arg Ala Lys Glu Leu Asn Ile Asp Val Val
                180                 185                 190

Gly Val Ser Phe His Val Gly Ser Gly Cys Thr Asp Pro Glu Thr Phe
                195                 200                 205

Val Gln Ala Ile Ser Asp Ala Arg Cys Val Phe Asp Met Gly Ala Glu
                210                 215                 220

Val Gly Phe Ser Met Tyr Leu Leu Asp Ile Gly Gly Gly Phe Pro Gly
225                 230                 235                 240

Ser Glu Asp Val Lys Leu Lys Phe Glu Glu Ile Thr Gly Val Ile Asn
                245                 250                 255

Pro Ala Leu Asp Lys Tyr Phe Pro Ser Asp Ser Gly Val Arg Ile Ile
                260                 265                 270

Ala Glu Pro Gly Arg Tyr Tyr Val Ala Ser Ala Phe Thr Leu Ala Val
                275                 280                 285
```

```
Asn Ile Ile Ala Lys Lys Ile Val Leu Lys Glu Gln Thr Gly Ser Asp
    290                 295                 300

Asp Glu Asp Glu Ser Ser Glu Gln Thr Phe Met Tyr Tyr Val Asn Asp
305                 310                 315                 320

Gly Val Tyr Gly Ser Phe Asn Cys Ile Leu Tyr Asp His Ala His Val
                325                 330                 335

Lys Pro Leu Leu Gln Lys Arg Pro Lys Pro Asp Glu Lys Tyr Tyr Ser
            340                 345                 350

Ser Ser Ile Trp Gly Pro Thr Cys Asp Gly Leu Asp Arg Ile Val Glu
        355                 360                 365

Arg Cys Asp Leu Pro Glu Met His Val Gly Asp Trp Met Leu Phe Glu
370                 375                 380

Asn Met Gly Ala Tyr Thr Val Ala Ala Ala Ser Thr Phe Asn Gly Phe
385                 390                 395                 400

Gln Arg Pro Thr Ile Tyr Tyr Val Met Ser Gly Pro Ala Trp Gln Leu
                405                 410                 415

Met Gln Gln Phe Gln Asn Pro Asp Phe Pro Pro Glu Val Glu Glu Gln
            420                 425                 430

Asp Ala Ser Thr Leu Pro Val Ser Cys Ala Trp Glu Ser Gly Met Lys
        435                 440                 445

Arg His Arg Ala Ala Cys Ala Ser Ala Ser Ile Asn Val
450                 455                 460

<210> SEQ ID NO 7
<211> LENGTH: 656
<212> TYPE: PRT
<213> ORGANISM: Homo sapiens

<400> SEQUENCE: 7

Met Ala Ser Thr Asp Tyr Ser Thr Tyr Ser Gln Ala Ala Ala Gln Gln
1               5                   10                  15

Gly Tyr Ser Ala Tyr Thr Ala Gln Pro Thr Gln Gly Tyr Ala Gln Thr
            20                  25                  30

Thr Gln Ala Tyr Gly Gln Gln Ser Tyr Gly Thr Tyr Gly Gln Pro Thr
        35                  40                  45

Asp Val Ser Tyr Thr Gln Ala Gln Thr Thr Ala Thr Tyr Gly Gln Thr
    50                  55                  60

Ala Tyr Ala Thr Ser Tyr Gly Gln Pro Pro Thr Gly Tyr Thr Thr Pro
65                  70                  75                  80

Thr Ala Pro Gln Ala Tyr Ser Gln Pro Val Gln Gly Tyr Gly Thr Gly
                85                  90                  95

Ala Tyr Asp Thr Thr Thr Ala Thr Val Thr Thr Thr Gln Ala Ser Tyr
            100                 105                 110

Ala Ala Gln Ser Ala Tyr Gly Thr Gln Pro Ala Tyr Pro Ala Tyr Gly
        115                 120                 125

Gln Gln Pro Ala Ala Thr Ala Pro Thr Arg Pro Gln Asp Gly Asn Lys
    130                 135                 140

Pro Thr Glu Thr Ser Gln Pro Gln Ser Ser Thr Gly Gly Tyr Asn Gln
145                 150                 155                 160

Pro Ser Leu Gly Tyr Gly Gln Ser Asn Tyr Ser Tyr Pro Gln Val Pro
                165                 170                 175

Gly Ser Tyr Pro Met Gln Pro Val Thr Ala Pro Pro Ser Tyr Pro Pro
            180                 185                 190

Thr Ser Tyr Ser Ser Thr Gln Pro Thr Ser Tyr Asp Gln Ser Ser Tyr
        195                 200                 205
```

-continued

```
Ser Gln Gln Asn Thr Tyr Gly Gln Pro Ser Ser Tyr Gly Gln Gln Ser
    210                 215                 220

Ser Tyr Gly Gln Gln Ser Ser Tyr Gly Gln Gln Pro Pro Thr Ser Tyr
225                 230                 235                 240

Pro Pro Gln Thr Gly Ser Tyr Ser Gln Ala Pro Ser Gln Tyr Ser Gln
                245                 250                 255

Gln Ser Ser Ser Tyr Gly Gln Gln Ser Ser Phe Arg Gln Asp His Pro
            260                 265                 270

Ser Ser Met Gly Val Tyr Gly Gln Glu Ser Gly Gly Phe Ser Gly Pro
        275                 280                 285

Gly Glu Asn Arg Ser Met Ser Gly Pro Asp Asn Arg Gly Arg Gly Arg
    290                 295                 300

Gly Gly Phe Asp Arg Gly Gly Met Ser Arg Gly Gly Arg Gly Gly Gly
305                 310                 315                 320

Arg Gly Gly Met Gly Ser Ala Gly Glu Arg Gly Gly Phe Asn Lys Pro
                325                 330                 335

Gly Gly Pro Met Asp Glu Gly Pro Asp Leu Asp Leu Gly Pro Pro Val
            340                 345                 350

Asp Pro Asp Glu Asp Ser Asp Asn Ser Ala Ile Tyr Val Gln Gly Leu
        355                 360                 365

Asn Asp Ser Val Thr Leu Asp Asp Leu Ala Asp Phe Phe Lys Gln Cys
    370                 375                 380

Gly Val Val Lys Met Asn Lys Arg Thr Gly Gln Pro Met Ile His Ile
385                 390                 395                 400

Tyr Leu Asp Lys Glu Thr Gly Lys Pro Lys Gly Asp Ala Thr Val Ser
                405                 410                 415

Tyr Glu Asp Pro Pro Thr Ala Lys Ala Ala Val Glu Trp Phe Asp Gly
            420                 425                 430

Lys Asp Phe Gln Gly Ser Lys Leu Lys Val Ser Leu Ala Arg Lys Lys
        435                 440                 445

Pro Pro Met Asn Ser Met Arg Gly Gly Leu Pro Pro Arg Glu Gly Arg
    450                 455                 460

Gly Met Pro Pro Pro Leu Arg Gly Gly Pro Gly Gly Pro Gly Gly Pro
465                 470                 475                 480

Gly Gly Pro Met Gly Arg Met Gly Gly Arg Gly Gly Asp Arg Gly Gly
                485                 490                 495

Phe Pro Pro Arg Gly Pro Arg Gly Ser Arg Gly Asn Pro Ser Gly Gly
            500                 505                 510

Gly Asn Val Gln His Arg Ala Gly Asp Trp Gln Cys Pro Asn Pro Gly
        515                 520                 525

Cys Gly Asn Gln Asn Phe Ala Trp Arg Thr Glu Cys Asn Gln Cys Lys
    530                 535                 540

Ala Pro Lys Pro Glu Gly Phe Leu Pro Pro Pro Phe Pro Pro Pro Gly
545                 550                 555                 560

Gly Asp Arg Gly Arg Gly Gly Pro Gly Gly Met Arg Gly Gly Arg Gly
                565                 570                 575

Gly Leu Met Asp Arg Gly Gly Pro Gly Gly Met Phe Arg Gly Gly Arg
            580                 585                 590

Gly Gly Asp Arg Gly Gly Phe Arg Gly Gly Arg Gly Met Asp Arg Gly
        595                 600                 605

Gly Phe Gly Gly Gly Arg Arg Gly Gly Pro Gly Gly Pro Pro Gly Pro
    610                 615                 620
```

```
Leu Met Glu Gln Met Gly Gly Arg Arg Gly Arg Gly Gly Pro Gly
625                 630                 635                 640

Lys Met Asp Lys Gly Glu His Arg Gln Glu Arg Arg Asp Arg Pro Tyr
        645                 650                 655

<210> SEQ ID NO 8
<211> LENGTH: 1052
<212> TYPE: PRT
<213> ORGANISM: Homo sapiens

<400> SEQUENCE: 8

Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
    50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
                85                  90                  95

Trp Leu His Val Asp Met Gly Val Ser Ser Val Arg Glu Lys Tyr Glu
            100                 105                 110

Leu Ala His Pro Pro Glu Glu Trp Lys Tyr Glu Leu Arg Ile Arg Tyr
        115                 120                 125

Leu Pro Lys Gly Phe Leu Asn Gln Phe Thr Glu Asp Lys Pro Thr Leu
    130                 135                 140

Asn Phe Phe Tyr Gln Gln Val Lys Ser Asp Tyr Met Leu Glu Ile Ala
145                 150                 155                 160

Asp Gln Val Asp Gln Glu Ile Ala Leu Lys Leu Gly Cys Leu Glu Ile
                165                 170                 175

Arg Arg Ser Tyr Trp Glu Met Arg Gly Asn Ala Leu Glu Lys Lys Ser
            180                 185                 190

Asn Tyr Glu Val Leu Glu Lys Asp Val Gly Leu Lys Arg Phe Phe Pro
        195                 200                 205

Lys Ser Leu Leu Asp Ser Val Lys Ala Lys Thr Leu Arg Lys Leu Ile
    210                 215                 220

Gln Gln Thr Phe Arg Gln Phe Ala Asn Leu Asn Arg Glu Glu Ser Ile
225                 230                 235                 240

Leu Lys Phe Phe Glu Ile Leu Ser Pro Val Tyr Arg Phe Asp Lys Glu
                245                 250                 255

Cys Phe Lys Cys Ala Leu Gly Ser Ser Trp Ile Ile Ser Val Glu Leu
            260                 265                 270

Ala Ile Gly Pro Glu Glu Gly Ile Ser Tyr Leu Thr Asp Lys Gly Cys
        275                 280                 285

Asn Pro Thr His Leu Ala Asp Phe Thr Gln Val Gln Thr Ile Gln Tyr
    290                 295                 300

Ser Asn Ser Glu Asp Lys Asp Arg Lys Gly Met Leu Gln Leu Lys Ile
305                 310                 315                 320

Ala Gly Ala Pro Glu Pro Leu Thr Val Thr Ala Pro Ser Leu Thr Ile
                325                 330                 335

Ala Glu Asn Met Ala Asp Leu Ile Asp Gly Tyr Cys Arg Leu Val Asn
            340                 345                 350
```

```
Gly Thr Ser Gln Ser Phe Ile Ile Arg Pro Gln Lys Glu Gly Glu Arg
            355                 360                 365

Ala Leu Pro Ser Ile Pro Lys Leu Ala Asn Ser Glu Lys Gln Gly Met
370                 375                 380

Arg Thr His Ala Val Ser Val Ser Glu Thr Asp Asp Tyr Ala Glu Ile
385                 390                 395                 400

Ile Asp Glu Glu Asp Thr Tyr Thr Met Pro Ser Thr Arg Asp Tyr Glu
                405                 410                 415

Ile Gln Arg Glu Arg Ile Glu Leu Gly Arg Cys Ile Gly Glu Gly Gln
                420                 425                 430

Phe Gly Asp Val His Gln Gly Ile Tyr Met Ser Pro Glu Asn Pro Ala
            435                 440                 445

Leu Ala Val Ala Ile Lys Thr Cys Lys Asn Cys Thr Ser Asp Ser Val
450                 455                 460

Arg Glu Lys Phe Leu Gln Glu Ala Leu Thr Met Arg Gln Phe Asp His
465                 470                 475                 480

Pro His Ile Val Lys Leu Ile Gly Val Ile Thr Glu Asn Pro Val Trp
                485                 490                 495

Ile Ile Met Glu Leu Cys Thr Leu Gly Glu Leu Arg Ser Phe Leu Gln
                500                 505                 510

Val Arg Lys Tyr Ser Leu Asp Leu Ala Ser Leu Ile Leu Tyr Ala Tyr
            515                 520                 525

Gln Leu Ser Thr Ala Leu Ala Tyr Leu Glu Ser Lys Arg Phe Val His
            530                 535                 540

Arg Asp Ile Ala Ala Arg Asn Val Leu Val Ser Ser Asn Asp Cys Val
545                 550                 555                 560

Lys Leu Gly Asp Phe Gly Leu Ser Arg Tyr Met Glu Asp Ser Thr Tyr
                565                 570                 575

Tyr Lys Ala Ser Lys Gly Lys Leu Pro Ile Lys Trp Met Ala Pro Glu
            580                 585                 590

Ser Ile Asn Phe Arg Arg Phe Thr Ser Ala Ser Asp Val Trp Met Phe
            595                 600                 605

Gly Val Cys Met Trp Glu Ile Leu Met His Gly Val Lys Pro Phe Gln
            610                 615                 620

Gly Val Lys Asn Asn Asp Val Ile Gly Arg Ile Glu Asn Gly Glu Arg
625                 630                 635                 640

Leu Pro Met Pro Pro Asn Cys Pro Pro Thr Leu Tyr Ser Leu Met Thr
                645                 650                 655

Lys Cys Trp Ala Tyr Asp Pro Ser Arg Arg Pro Arg Phe Thr Glu Leu
                660                 665                 670

Lys Ala Gln Leu Ser Thr Ile Leu Glu Glu Glu Lys Ala Gln Gln Glu
            675                 680                 685

Glu Arg Met Arg Met Glu Ser Arg Arg Gln Ala Thr Val Ser Trp Asp
690                 695                 700

Ser Gly Gly Ser Asp Glu Ala Pro Pro Lys Pro Ser Arg Pro Gly Tyr
705                 710                 715                 720

Pro Ser Pro Arg Ser Ser Glu Gly Phe Tyr Pro Ser Pro Gln His Met
                725                 730                 735

Val Gln Thr Asn His Tyr Gln Val Ser Gly Tyr Pro Gly Ser His Gly
            740                 745                 750

Ile Thr Ala Met Ala Gly Ser Ile Tyr Pro Gly Gln Ala Ser Leu Leu
            755                 760                 765
```

```
Asp Gln Thr Asp Ser Trp Asn His Arg Pro Gln Glu Ile Ala Met Trp
    770                 775                 780

Gln Pro Asn Val Glu Asp Ser Thr Val Leu Asp Leu Arg Gly Ile Gly
785                 790                 795                 800

Gln Val Leu Pro Thr His Leu Met Glu Glu Arg Leu Ile Arg Gln Gln
            805                 810                 815

Gln Glu Met Glu Glu Asp Gln Arg Trp Leu Glu Lys Glu Glu Arg Phe
        820                 825                 830

Leu Lys Pro Asp Val Arg Leu Ser Arg Gly Ser Ile Asp Arg Glu Asp
            835                 840                 845

Gly Ser Leu Gln Gly Pro Ile Gly Asn Gln His Ile Tyr Gln Pro Val
850                 855                 860

Gly Lys Pro Asp Pro Ala Ala Pro Pro Lys Lys Pro Pro Arg Pro Gly
865                 870                 875                 880

Ala Pro Gly His Leu Gly Ser Leu Ala Ser Leu Ser Ser Pro Ala Asp
                885                 890                 895

Ser Tyr Asn Glu Gly Val Lys Leu Gln Pro Gln Glu Ile Ser Pro Pro
            900                 905                 910

Pro Thr Ala Asn Leu Asp Arg Ser Asn Asp Lys Val Tyr Glu Asn Val
        915                 920                 925

Thr Gly Leu Val Lys Ala Val Ile Glu Met Ser Ser Lys Ile Gln Pro
930                 935                 940

Ala Pro Pro Glu Glu Tyr Val Pro Met Val Lys Glu Val Gly Leu Ala
945                 950                 955                 960

Leu Arg Thr Leu Leu Ala Thr Val Asp Glu Thr Ile Pro Leu Leu Pro
                965                 970                 975

Ala Ser Thr His Arg Glu Ile Glu Met Ala Gln Lys Leu Leu Asn Ser
            980                 985                 990

Asp Leu Gly Glu Leu Ile Asn Lys Met Lys Leu Ala Gln Gln Tyr Val
        995                 1000                1005

Met Thr Ser Leu Gln Gln Glu Tyr Lys Lys Gln Met Leu Thr Ala
    1010                1015                1020

Ala His Ala Leu Ala Val Asp Ala Lys Asn Leu Leu Asp Val Ile
    1025                1030                1035

Asp Gln Ala Arg Leu Lys Met Leu Gly Gln Thr Arg Pro His
    1040                1045                1050

<210> SEQ ID NO 9
<211> LENGTH: 197
<212> TYPE: PRT
<213> ORGANISM: Homo sapiens
<220> FEATURE:
<221> NAME/KEY: MISC_FEATURE
<222> LOCATION: (73)..(73)
<223> OTHER INFORMATION: X = selenocysteine (U)

<400> SEQUENCE: 9

Met Ser Leu Gly Arg Leu Cys Arg Leu Leu Lys Pro Ala Leu Leu Cys
1               5                   10                  15

Gly Ala Leu Ala Ala Pro Gly Leu Ala Gly Thr Met Cys Ala Ser Arg
            20                  25                  30

Asp Asp Trp Arg Cys Ala Arg Ser Met His Glu Phe Ser Ala Lys Asp
        35                  40                  45

Ile Asp Gly His Met Val Asn Leu Asp Lys Tyr Arg Gly Phe Val Cys
    50                  55                  60

Ile Val Thr Asn Val Ala Ser Gln Xaa Gly Lys Thr Glu Val Asn Tyr
```

```
                65                  70                  75                  80
        Thr Gln Leu Val Asp Leu His Ala Arg Tyr Ala Glu Cys Gly Leu Arg
                            85                  90                  95

Ile Leu Ala Phe Pro Cys Asn Gln Phe Gly Lys Gln Glu Pro Gly Ser
                           100                 105                 110

Asn Glu Glu Ile Lys Glu Phe Ala Ala Gly Tyr Asn Val Lys Phe Asp
                       115                 120                 125

Met Phe Ser Lys Ile Cys Val Asn Gly Asp Asp Ala His Pro Leu Trp
                   130                 135                 140

Lys Trp Met Lys Ile Gln Pro Lys Gly Lys Gly Ile Leu Gly Asn Ala
        145                 150                 155                 160

Ile Lys Trp Asn Phe Thr Lys Phe Leu Ile Asp Lys Asn Gly Cys Val
                           165                 170                 175

Val Lys Arg Tyr Gly Pro Met Glu Glu Pro Leu Val Ile Glu Lys Asp
                       180                 185                 190

Leu Pro His Tyr Phe
                       195

<210> SEQ ID NO 10
<211> LENGTH: 209
<212> TYPE: PRT
<213> ORGANISM: Homo sapiens

<400> SEQUENCE: 10

Met Gly Lys Gly Asp Pro Asn Lys Pro Arg Gly Lys Met Ser Ser Tyr
        1               5                   10                  15

Ala Phe Phe Val Gln Thr Cys Arg Glu Glu His Lys Lys Lys His Pro
                        20                  25                  30

Asp Ser Ser Val Asn Phe Ala Glu Phe Ser Lys Lys Cys Ser Glu Arg
                    35                  40                  45

Trp Lys Thr Met Ser Ala Lys Glu Lys Ser Lys Phe Glu Asp Met Ala
                50                  55                  60

Lys Ser Asp Lys Ala Arg Tyr Asp Arg Glu Met Lys Asn Tyr Val Pro
        65                  70                  75                  80

Pro Lys Gly Asp Lys Lys Gly Lys Lys Lys Asp Pro Asn Ala Pro Lys
                        85                  90                  95

Arg Pro Pro Ser Ala Phe Phe Leu Phe Cys Ser Glu His Arg Pro Lys
                    100                 105                 110

Ile Lys Ser Glu His Pro Gly Leu Ser Ile Gly Asp Thr Ala Lys Lys
                115                 120                 125

Leu Gly Glu Met Trp Ser Glu Gln Ser Ala Lys Asp Lys Gln Pro Tyr
            130                 135                 140

Glu Gln Lys Ala Ala Lys Leu Lys Glu Lys Tyr Glu Lys Asp Ile Ala
        145                 150                 155                 160

Ala Tyr Arg Ala Lys Gly Lys Ser Glu Ala Gly Lys Lys Gly Pro Gly
                        165                 170                 175

Arg Pro Thr Gly Ser Lys Lys Lys Asn Glu Pro Glu Asp Glu Glu Glu
                    180                 185                 190

Glu Glu Glu Glu Glu Asp Glu Asp Glu Glu Glu Asp Glu Asp Glu Glu
                195                 200                 205

Glu

<210> SEQ ID NO 11
<211> LENGTH: 153
<212> TYPE: PRT
```

<213> ORGANISM: Homo sapiens

<400> SEQUENCE: 11

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
            20                  25                  30

Phe Tyr Leu Ala Leu Cys Leu Leu Thr Phe Thr Ser Ser Ala Thr Ala
                35                  40                  45

Gly Pro Glu Thr Leu Cys Gly Ala Glu Leu Val Asp Ala Leu Gln Phe
            50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Glu Val His Leu Lys Asn Ala Ser Arg Gly
            130                 135                 140

Ser Ala Gly Asn Lys Asn Tyr Arg Met
145                 150

<210> SEQ ID NO 12
<211> LENGTH: 1338
<212> TYPE: PRT
<213> ORGANISM: Homo sapiens

<400> SEQUENCE: 12

Met Ala Ser Pro Pro Arg His Gly Pro Pro Gly Pro Ala Ser Gly Asp
1               5                   10                  15

Gly Pro Asn Leu Asn Asn Asn Asn Asn Asn Asn His Ser Val Arg
            20                  25                  30

Lys Cys Gly Tyr Leu Arg Lys Gln Lys His Gly His Lys Arg Phe Phe
            35                  40                  45

Val Leu Arg Gly Pro Gly Ala Gly Gly Asp Glu Ala Thr Ala Gly Gly
50                  55                  60

Gly Ser Ala Pro Gln Pro Pro Arg Leu Glu Tyr Tyr Glu Ser Glu Lys
65                  70                  75                  80

Lys Trp Arg Ser Lys Ala Gly Ala Pro Lys Arg Val Ile Ala Leu Asp
                85                  90                  95

Cys Cys Leu Asn Ile Asn Lys Arg Ala Asp Ala Lys His Lys Tyr Leu
            100                 105                 110

Ile Ala Leu Tyr Thr Lys Asp Glu Tyr Phe Ala Val Ala Ala Glu Asn
            115                 120                 125

Glu Gln Glu Gln Glu Gly Trp Tyr Arg Ala Leu Thr Asp Leu Val Ser
            130                 135                 140

Glu Gly Arg Ala Ala Ala Gly Asp Ala Pro Ala Ala Pro Ala
145                 150                 155                 160

Ala Ser Cys Ser Ala Ser Leu Pro Gly Leu Gly Gly Ser Ala Gly
                165                 170                 175

Ala Ala Gly Ala Glu Asp Ser Tyr Gly Leu Val Ala Pro Ala Thr Ala
            180                 185                 190

Ala Tyr Arg Glu Val Trp Gln Val Asn Leu Lys Pro Lys Gly Leu Gly

-continued

```
            195                 200                 205
Gln Ser Lys Asn Leu Thr Gly Val Tyr Arg Leu Cys Leu Ser Ala Arg
    210                 215                 220

Thr Ile Gly Phe Val Lys Leu Asn Cys Glu Gln Pro Ser Val Thr Leu
225                 230                 235                 240

Gln Leu Met Asn Ile Arg Arg Cys Gly His Ser Asp Ser Phe Phe Phe
                245                 250                 255

Ile Glu Val Gly Arg Ser Ala Val Thr Gly Pro Gly Glu Leu Trp Met
                260                 265                 270

Gln Ala Asp Asp Ser Val Val Ala Gln Asn Ile His Glu Thr Ile Leu
            275                 280                 285

Glu Ala Met Lys Ala Leu Lys Glu Leu Phe Glu Phe Arg Pro Arg Ser
    290                 295                 300

Lys Ser Gln Ser Ser Gly Ser Ser Ala Thr His Pro Ile Ser Val Pro
305                 310                 315                 320

Gly Ala Arg Arg His His His Leu Val Asn Leu Pro Pro Ser Gln Thr
                325                 330                 335

Gly Leu Val Arg Arg Ser Arg Thr Asp Ser Leu Ala Ala Thr Pro Pro
                340                 345                 350

Ala Ala Lys Cys Ser Ser Cys Arg Val Arg Thr Ala Ser Glu Gly Asp
            355                 360                 365

Gly Gly Ala Ala Ala Gly Ala Ala Ala Gly Ala Arg Pro Val Ser
    370                 375                 380

Val Ala Gly Ser Pro Leu Ser Pro Gly Pro Val Arg Ala Pro Leu Ser
385                 390                 395                 400

Arg Ser His Thr Leu Ser Gly Gly Cys Gly Gly Arg Gly Ser Lys Val
                405                 410                 415

Ala Leu Leu Pro Ala Gly Gly Ala Leu Gln His Ser Arg Ser Met Ser
                420                 425                 430

Met Pro Val Ala His Ser Pro Ala Ala Thr Ser Pro Gly Ser Leu
            435                 440                 445

Ser Ser Ser Ser Gly His Gly Ser Gly Ser Tyr Pro Pro Pro Gly
    450                 455                 460

Pro His Pro Pro Leu Pro His Pro Leu His His Gly Pro Gly Gln Arg
465                 470                 475                 480

Pro Ser Ser Gly Ser Ala Ser Ala Ser Gly Ser Pro Ser Asp Pro Gly
                485                 490                 495

Phe Met Ser Leu Asp Glu Tyr Gly Ser Ser Pro Gly Asp Leu Arg Ala
                500                 505                 510

Phe Cys Ser His Arg Ser Asn Thr Pro Glu Ser Ile Ala Glu Thr Pro
            515                 520                 525

Pro Ala Arg Asp Gly Gly Gly Gly Glu Phe Tyr Gly Tyr Met Thr
    530                 535                 540

Met Asp Arg Pro Leu Ser His Cys Gly Arg Ser Tyr Arg Arg Val Ser
545                 550                 555                 560

Gly Asp Ala Ala Gln Asp Leu Asp Arg Gly Leu Arg Lys Arg Thr Tyr
                565                 570                 575

Ser Leu Thr Thr Pro Ala Arg Gln Arg Pro Val Pro Gln Pro Ser Ser
                580                 585                 590

Ala Ser Leu Asp Glu Tyr Thr Leu Met Arg Ala Thr Phe Ser Gly Ser
            595                 600                 605

Ala Gly Arg Leu Cys Pro Ser Cys Pro Ala Ser Ser Pro Lys Val Ala
    610                 615                 620
```

```
Tyr His Pro Tyr Pro Glu Asp Tyr Gly Asp Ile Glu Ile Gly Ser His
625                 630                 635                 640

Arg Ser Ser Ser Ser Asn Leu Gly Ala Asp Asp Gly Tyr Met Pro Met
                645                 650                 655

Thr Pro Gly Ala Ala Leu Ala Gly Ser Gly Ser Gly Ser Cys Arg Ser
        660                 665                 670

Asp Asp Tyr Met Pro Met Ser Pro Ala Ser Val Ser Ala Pro Lys Gln
            675                 680                 685

Ile Leu Gln Pro Arg Ala Ala Ala Ala Ala Ala Val Pro Ser
690                 695                 700

Ala Gly Pro Ala Gly Pro Ala Pro Thr Ser Ala Ala Gly Arg Thr Phe
705                 710                 715                 720

Pro Ala Ser Gly Gly Gly Tyr Lys Ala Ser Ser Pro Ala Glu Ser Ser
                725                 730                 735

Pro Glu Asp Ser Gly Tyr Met Arg Met Trp Cys Gly Ser Lys Leu Ser
            740                 745                 750

Met Glu His Ala Asp Gly Lys Leu Leu Pro Asn Gly Asp Tyr Leu Asn
            755                 760                 765

Val Ser Pro Ser Asp Ala Val Thr Thr Gly Thr Pro Pro Asp Phe Phe
770                 775                 780

Ser Ala Ala Leu His Pro Gly Gly Glu Pro Leu Arg Gly Val Pro Gly
785                 790                 795                 800

Cys Cys Tyr Ser Ser Leu Pro Arg Ser Tyr Lys Ala Pro Tyr Thr Cys
                805                 810                 815

Gly Gly Asp Ser Asp Gln Tyr Val Leu Met Ser Ser Pro Val Gly Arg
            820                 825                 830

Ile Leu Glu Glu Glu Arg Leu Glu Pro Gln Ala Thr Pro Gly Pro Ser
            835                 840                 845

Gln Ala Ala Ser Ala Phe Gly Ala Gly Pro Thr Gln Pro Pro His Pro
850                 855                 860

Val Val Pro Ser Pro Val Arg Pro Ser Gly Gly Arg Pro Glu Gly Phe
865                 870                 875                 880

Leu Gly Gln Arg Gly Arg Ala Val Arg Pro Thr Arg Leu Ser Leu Glu
                885                 890                 895

Gly Leu Pro Ser Leu Pro Ser Met His Glu Tyr Pro Leu Pro Pro Glu
            900                 905                 910

Pro Lys Ser Pro Gly Glu Tyr Ile Asn Ile Asp Phe Gly Glu Pro Gly
    915                 920                 925

Ala Arg Leu Ser Pro Pro Ala Pro Pro Leu Leu Ala Ser Ala Ala Ser
            930                 935                 940

Ser Ser Ser Leu Leu Ser Ala Ser Ser Pro Ala Ser Ser Leu Gly Ser
945                 950                 955                 960

Gly Thr Pro Gly Thr Ser Ser Asp Ser Arg Gln Arg Ser Pro Leu Ser
                965                 970                 975

Asp Tyr Met Asn Leu Asp Phe Ser Ser Pro Lys Ser Pro Lys Pro Gly
            980                 985                 990

Ala Pro Ser Gly His Pro Val Gly Ser Leu Asp Gly Leu Leu Ser Pro
            995                 1000                1005

Glu Ala Ser Ser Pro Tyr Pro Pro Leu Pro Pro Arg Pro Ser Ala
    1010                1015                1020

Ser Pro Ser Ser Ser Leu Gln Pro Pro Pro Pro Pro Ala Pro
    1025                1030                1035
```

```
Gly Glu Leu Tyr Arg Leu Pro Pro Ala Ser Ala Val Ala Thr Ala
    1040            1045                1050

Gln Gly Pro Gly Ala Ala Ser Ser Leu Ser Asp Thr Gly Asp
    1055            1060                1065

Asn Gly Asp Tyr Thr Glu Met Ala Phe Gly Val Ala Ala Thr Pro
    1070            1075                1080

Pro Gln Pro Ile Ala Ala Pro Pro Lys Pro Glu Ala Ala Arg Val
    1085            1090                1095

Ala Ser Pro Thr Ser Gly Val Lys Arg Leu Ser Leu Met Glu Gln
    1100            1105                1110

Val Ser Gly Val Glu Ala Phe Leu Gln Ala Ser Gln Pro Pro Asp
    1115            1120                1125

Pro His Arg Gly Ala Lys Val Ile Arg Ala Asp Pro Gln Gly Gly
    1130            1135                1140

Arg Arg Arg His Ser Ser Glu Thr Phe Ser Ser Thr Thr Thr Val
    1145            1150                1155

Thr Pro Val Ser Pro Ser Phe Ala His Asn Pro Lys Arg His Asn
    1160            1165                1170

Ser Ala Ser Val Glu Asn Val Ser Leu Arg Lys Ser Ser Glu Gly
    1175            1180                1185

Gly Val Gly Val Gly Pro Gly Gly Gly Asp Glu Pro Pro Thr Ser
    1190            1195                1200

Pro Arg Gln Leu Gln Pro Ala Pro Pro Leu Ala Pro Gln Gly Arg
    1205            1210                1215

Pro Trp Thr Pro Gly Gln Pro Gly Gly Leu Val Gly Cys Pro Gly
    1220            1225                1230

Ser Gly Gly Ser Pro Met Arg Arg Glu Thr Ser Ala Gly Phe Gln
    1235            1240                1245

Asn Gly Leu Asn Tyr Ile Ala Ile Asp Val Arg Glu Glu Pro Gly
    1250            1255                1260

Leu Pro Pro Gln Pro Gln Pro Pro Pro Pro Leu Pro Gln Pro
    1265            1270                1275

Gly Asp Lys Ser Ser Trp Gly Arg Thr Arg Ser Leu Gly Gly Leu
    1280            1285                1290

Ile Ser Ala Val Gly Val Gly Ser Thr Gly Gly Cys Gly Gly
    1295            1300                1305

Pro Gly Pro Gly Ala Leu Pro Pro Ala Asn Thr Tyr Ala Ser Ile
    1310            1315                1320

Asp Phe Leu Ser His His Leu Lys Glu Ala Thr Ile Val Lys Glu
    1325            1330                1335

<210> SEQ ID NO 13
<211> LENGTH: 483
<212> TYPE: PRT
<213> ORGANISM: Homo sapiens

<400> SEQUENCE: 13

Met Ser Ile Arg Val Thr Gln Lys Ser Tyr Lys Val Ser Thr Ser Gly
1               5                   10                  15

Pro Arg Ala Phe Ser Ser Arg Ser Tyr Thr Ser Gly Pro Gly Ser Arg
                20                  25                  30

Ile Ser Ser Ser Ser Phe Ser Arg Val Gly Ser Ser Asn Phe Arg Gly
            35                  40                  45

Gly Leu Gly Gly Gly Tyr Gly Gly Ala Ser Gly Met Gly Gly Ile Thr
        50                  55                  60
```

```
Ala Val Thr Val Asn Gln Ser Leu Leu Ser Pro Leu Val Leu Glu Val
 65                  70                  75                  80

Asp Pro Asn Ile Gln Ala Val Arg Thr Gln Glu Lys Glu Gln Ile Lys
                 85                  90                  95

Thr Leu Asn Asn Lys Phe Ala Ser Phe Ile Asp Lys Val Arg Phe Leu
            100                 105                 110

Glu Gln Gln Asn Lys Met Leu Glu Thr Lys Trp Ser Leu Leu Gln Gln
            115                 120                 125

Gln Lys Thr Ala Arg Ser Asn Met Asp Asn Met Phe Glu Ser Tyr Ile
        130                 135                 140

Asn Asn Leu Arg Arg Gln Leu Glu Thr Leu Gly Gln Glu Lys Leu Lys
145                 150                 155                 160

Leu Glu Ala Glu Leu Gly Asn Met Gln Gly Leu Val Glu Asp Phe Lys
                165                 170                 175

Asn Lys Tyr Glu Asp Glu Ile Asn Lys Arg Thr Glu Met Glu Asn Glu
            180                 185                 190

Phe Val Leu Ile Lys Lys Asp Val Asp Glu Ala Tyr Met Asn Lys Val
            195                 200                 205

Glu Leu Glu Ser Arg Leu Glu Gly Leu Thr Asp Glu Ile Asn Phe Leu
210                 215                 220

Arg Gln Leu Tyr Glu Glu Glu Ile Arg Glu Leu Gln Ser Gln Ile Ser
225                 230                 235                 240

Asp Thr Ser Val Val Leu Ser Met Asp Asn Ser Arg Ser Leu Asp Met
                245                 250                 255

Asp Ser Ile Ile Ala Glu Val Lys Ala Gln Tyr Glu Asp Ile Ala Asn
            260                 265                 270

Arg Ser Arg Ala Glu Ala Glu Ser Met Tyr Gln Ile Lys Tyr Glu Glu
            275                 280                 285

Leu Gln Ser Leu Ala Gly Lys His Gly Asp Asp Leu Arg Arg Thr Lys
            290                 295                 300

Thr Glu Ile Ser Glu Met Asn Arg Asn Ile Ser Arg Leu Gln Ala Glu
305                 310                 315                 320

Ile Glu Gly Leu Lys Gly Gln Arg Ala Ser Leu Glu Ala Ala Ile Ala
                325                 330                 335

Asp Ala Glu Gln Arg Gly Glu Leu Ala Ile Lys Asp Ala Asn Ala Lys
            340                 345                 350

Leu Ser Glu Leu Glu Ala Ala Leu Gln Arg Ala Lys Gln Asp Met Ala
            355                 360                 365

Arg Gln Leu Arg Glu Tyr Gln Glu Leu Met Asn Val Lys Leu Ala Leu
            370                 375                 380

Asp Ile Glu Ile Ala Thr Tyr Arg Lys Leu Leu Glu Gly Glu Glu Ser
385                 390                 395                 400

Arg Leu Glu Ser Gly Met Gln Asn Met Ser Ile His Thr Lys Thr Thr
                405                 410                 415

Ser Gly Tyr Ala Gly Gly Leu Ser Ser Ala Tyr Gly Gly Leu Thr Ser
            420                 425                 430

Pro Gly Leu Ser Tyr Ser Leu Gly Ser Ser Phe Gly Ser Gly Ala Gly
            435                 440                 445

Ser Ser Ser Phe Ser Arg Thr Ser Ser Ser Arg Ala Val Val Val Lys
            450                 455                 460

Lys Ile Glu Thr Arg Asp Gly Lys Leu Val Ser Glu Ser Ser Asp Val
465                 470                 475                 480
```

Leu Pro Lys

<210> SEQ ID NO 14
<211> LENGTH: 372
<212> TYPE: PRT
<213> ORGANISM: Homo sapiens

<400> SEQUENCE: 14

Met Ile Phe Pro Trp Lys Cys Gln Ser Thr Gln Arg Asp Leu Trp Asn
1               5                   10                  15

Ile Phe Lys Leu Trp Gly Trp Thr Met Leu Cys Cys Asp Phe Leu Ala
            20                  25                  30

His His Gly Thr Asp Cys Trp Thr Tyr His Tyr Ser Glu Lys Pro Met
        35                  40                  45

Asn Trp Gln Arg Ala Arg Arg Phe Cys Arg Asp Asn Tyr Thr Asp Leu
    50                  55                  60

Val Ala Ile Gln Asn Lys Ala Glu Ile Glu Tyr Leu Glu Lys Thr Leu
65                  70                  75                  80

Pro Phe Ser Arg Ser Tyr Tyr Trp Ile Gly Ile Arg Lys Ile Gly Gly
                85                  90                  95

Ile Trp Thr Trp Val Gly Thr Asn Lys Ser Leu Thr Glu Glu Ala Glu
            100                 105                 110

Asn Trp Gly Asp Gly Glu Pro Asn Asn Lys Lys Asn Lys Glu Asp Cys
        115                 120                 125

Val Glu Ile Tyr Ile Lys Arg Asn Lys Asp Ala Gly Lys Trp Asn Asp
130                 135                 140

Asp Ala Cys His Lys Leu Lys Ala Ala Leu Cys Tyr Thr Ala Ser Cys
145                 150                 155                 160

Gln Pro Trp Ser Cys Ser Gly His Gly Glu Cys Val Glu Ile Ile Asn
                165                 170                 175

Asn Tyr Thr Cys Asn Cys Asp Val Gly Tyr Tyr Gly Pro Gln Cys Gln
            180                 185                 190

Phe Val Ile Gln Cys Glu Pro Leu Glu Ala Pro Glu Leu Gly Thr Met
        195                 200                 205

Asp Cys Thr His Pro Leu Gly Asn Phe Ser Phe Ser Ser Gln Cys Ala
210                 215                 220

Phe Ser Cys Ser Glu Gly Thr Asn Leu Thr Gly Ile Glu Glu Thr Thr
225                 230                 235                 240

Cys Gly Pro Phe Gly Asn Trp Ser Ser Pro Glu Pro Thr Cys Gln Val
                245                 250                 255

Ile Gln Cys Glu Pro Leu Ser Ala Pro Asp Leu Gly Ile Met Asn Cys
            260                 265                 270

Ser His Pro Leu Ala Ser Phe Ser Phe Thr Ser Ala Cys Thr Phe Ile
        275                 280                 285

Cys Ser Glu Gly Thr Glu Leu Ile Gly Lys Lys Lys Thr Ile Cys Glu
        290                 295                 300

Ser Ser Gly Ile Trp Ser Asn Pro Ser Pro Ile Cys Gln Lys Leu Asp
305                 310                 315                 320

Lys Ser Phe Ser Met Ile Lys Glu Gly Asp Tyr Asn Pro Leu Phe Ile
                325                 330                 335

Pro Val Ala Val Met Val Thr Ala Phe Ser Gly Leu Ala Phe Ile Ile
            340                 345                 350

Trp Leu Ala Arg Arg Leu Lys Lys Gly Lys Lys Ser Lys Arg Ser Met
        355                 360                 365

```
Asn Asp Pro Tyr
    370

<210> SEQ ID NO 15
<211> LENGTH: 209
<212> TYPE: PRT
<213> ORGANISM: Homo sapiens

<400> SEQUENCE: 15

Met Glu Leu Asn Ser Leu Leu Ile Leu Leu Glu Ala Ala Glu Tyr Leu
1               5                   10                  15

Glu Arg Arg Asp Arg Glu Ala Glu His Gly Tyr Ala Ser Val Leu Pro
            20                  25                  30

Phe Asp Gly Asp Phe Ala Arg Glu Lys Thr Lys Ala Ala Gly Leu Val
        35                  40                  45

Arg Lys Ala Pro Asn Asn Arg Ser Ser His Asn Glu Leu Glu Lys His
    50                  55                  60

Arg Arg Ala Lys Leu Arg Leu Tyr Leu Glu Gln Leu Lys Gln Leu Val
65                  70                  75                  80

Pro Leu Gly Pro Asp Ser Thr Arg His Thr Thr Leu Ser Leu Leu Lys
                85                  90                  95

Arg Ala Lys Val His Ile Lys Lys Leu Glu Glu Gln Asp Arg Arg Ala
            100                 105                 110

Leu Ser Ile Lys Glu Gln Leu Gln Gln Glu His Arg Phe Leu Lys Arg
        115                 120                 125

Arg Leu Glu Gln Leu Ser Val Gln Ser Val Arg Val Arg Thr Asp
    130                 135                 140

Ser Thr Gly Ser Ala Val Ser Thr Asp Asp Ser Gln Glu Val Asp
145                 150                 155                 160

Ile Glu Gly Met Glu Phe Gly Pro Gly Glu Leu Asp Ser Val Gly Ser
                165                 170                 175

Ser Ser Asp Ala Asp Asp His Tyr Ser Leu Gln Ser Gly Thr Gly Gly
            180                 185                 190

Asp Ser Gly Phe Gly Pro His Cys Arg Arg Leu Gly Arg Pro Ala Leu
        195                 200                 205

Ser

<210> SEQ ID NO 16
<211> LENGTH: 600
<212> TYPE: PRT
<213> ORGANISM: Homo sapiens

<400> SEQUENCE: 16

Met Gly Lys Lys Leu Asp Leu Ser Lys Leu Thr Asp Glu Glu Ala Gln
1               5                   10                  15

His Val Leu Glu Val Val Gln Arg Asp Phe Asp Leu Arg Arg Lys Glu
            20                  25                  30

Glu Glu Arg Leu Glu Ala Leu Lys Gly Lys Ile Lys Lys Glu Ser Ser
        35                  40                  45

Lys Arg Glu Leu Leu Ser Asp Thr Ala His Leu Asn Glu Thr His Cys
    50                  55                  60

Ala Arg Cys Leu Gln Pro Tyr Gln Leu Leu Val Asn Ser Lys Arg Gln
65                  70                  75                  80

Cys Leu Glu Cys Gly Leu Phe Thr Cys Lys Ser Cys Gly Arg Val His
                85                  90                  95

Pro Glu Glu Gln Gly Trp Ile Cys Asp Pro Cys His Leu Ala Arg Val
```

```
                100             105             110
Val Lys Ile Gly Ser Leu Glu Trp Tyr Tyr Glu His Val Lys Ala Arg
            115             120             125
Phe Lys Arg Phe Gly Ser Ala Lys Val Ile Arg Ser Leu His Gly Arg
        130             135             140
Leu Gln Gly Gly Ala Gly Pro Glu Leu Ile Ser Glu Glu Arg Ser Gly
145             150             155             160
Asp Ser Asp Gln Thr Asp Glu Asp Gly Glu Pro Gly Ser Glu Ala Gln
                165             170             175
Ala Gln Ala Gln Pro Phe Gly Ser Lys Lys Arg Leu Leu Ser Val
            180             185             190
His Asp Phe Asp Phe Glu Gly Asp Ser Asp Asp Ser Thr Gln Pro Gln
        195             200             205
Gly His Ser Leu His Leu Ser Ser Val Pro Glu Ala Arg Asp Ser Pro
    210             215             220
Gln Ser Leu Thr Asp Glu Ser Cys Ser Glu Lys Ala Ala Pro His Lys
225             230             235             240
Ala Glu Gly Leu Glu Glu Ala Asp Thr Gly Ala Ser Gly Cys His Ser
            245             250             255
His Pro Glu Glu Gln Pro Thr Ser Ile Ser Pro Ser Arg His Gly Ala
        260             265             270
Leu Ala Glu Leu Cys Pro Pro Gly Gly Ser His Arg Met Ala Leu Gly
    275             280             285
Thr Ala Ala Ala Leu Gly Ser Asn Val Ile Arg Asn Glu Gln Leu Pro
290             295             300
Leu Gln Tyr Leu Ala Asp Val Asp Thr Ser Asp Glu Glu Ser Ile Arg
305             310             315             320
Ala His Val Met Ala Ser His His Ser Lys Arg Gly Arg Ala Ser
            325             330             335
Ser Glu Ser Gln Ile Phe Glu Leu Asn Lys His Ile Ser Ala Val Glu
        340             345             350
Cys Leu Leu Thr Tyr Leu Glu Asn Thr Val Pro Pro Leu Ala Lys
    355             360             365
Gly Leu Gly Ala Gly Val Arg Thr Glu Ala Asp Val Glu Glu Ala
370             375             380
Leu Arg Arg Lys Leu Glu Glu Leu Thr Ser Asn Val Ser Asp Gln Glu
385             390             395             400
Thr Ser Ser Glu Glu Glu Glu Ala Lys Asp Glu Lys Ala Glu Pro Asn
            405             410             415
Arg Asp Lys Ser Val Gly Pro Leu Pro Gln Ala Asp Pro Glu Val Gly
        420             425             430
Thr Ala Ala His Gln Thr Asn Arg Gln Glu Lys Ser Pro Gln Asp Pro
    435             440             445
Gly Asp Pro Val Gln Tyr Asn Arg Thr Thr Asp Glu Glu Leu Ser Glu
    450             455             460
Leu Glu Asp Arg Val Ala Val Thr Ala Ser Glu Val Gln Gln Ala Glu
465             470             475             480
Ser Glu Val Ser Asp Ile Glu Ser Arg Ile Ala Ala Leu Arg Ala Ala
            485             490             495
Gly Leu Thr Val Lys Pro Ser Gly Lys Pro Arg Arg Lys Ser Asn Leu
        500             505             510
Pro Ile Phe Leu Pro Arg Val Ala Gly Lys Leu Gly Lys Arg Pro Glu
    515             520             525
```

Asp Pro Asn Ala Asp Pro Ser Ser Glu Ala Lys Ala Met Ala Val Pro
    530                 535                 540

Tyr Leu Leu Arg Arg Lys Phe Ser Asn Ser Leu Lys Ser Gln Gly Lys
545                 550                 555                 560

Asp Asp Asp Ser Phe Asp Arg Lys Ser Val Tyr Arg Gly Ser Leu Thr
                565                 570                 575

Gln Arg Asn Pro Asn Ala Arg Lys Gly Met Ala Ser His Thr Phe Ala
                580                 585                 590

Lys Pro Val Val Ala His Gln Ser
            595                 600

<210> SEQ ID NO 17
<211> LENGTH: 367
<212> TYPE: PRT
<213> ORGANISM: Homo sapiens

<400> SEQUENCE: 17

Met Ser Ser Pro Pro Ala Arg Ser Gly Phe Tyr Arg Gln Glu Val
1               5                   10                  15

Thr Lys Thr Ala Trp Glu Val Arg Ala Val Tyr Arg Asp Leu Gln Pro
                20                  25                  30

Val Gly Ser Gly Ala Tyr Gly Ala Val Cys Ser Ala Val Asp Gly Arg
            35                  40                  45

Thr Gly Ala Lys Val Ala Ile Lys Lys Leu Tyr Arg Pro Phe Gln Ser
        50                  55                  60

Glu Leu Phe Ala Lys Arg Ala Tyr Arg Glu Leu Arg Leu Leu Lys His
65                  70                  75                  80

Met Arg His Glu Asn Val Ile Gly Leu Leu Asp Val Phe Thr Pro Asp
                85                  90                  95

Glu Thr Leu Asp Asp Phe Thr Asp Phe Tyr Leu Val Met Pro Phe Met
                100                 105                 110

Gly Thr Asp Leu Gly Lys Leu Met Lys His Glu Lys Leu Gly Glu Asp
            115                 120                 125

Arg Ile Gln Phe Leu Val Tyr Gln Met Leu Lys Gly Leu Arg Tyr Ile
130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
            180                 185                 190

Ala Pro Glu Val Ile Leu Asn Trp Met Arg Tyr Thr Gln Thr Val Asp
        195                 200                 205

Ile Trp Ser Val Gly Cys Ile Met Ala Glu Met Ile Thr Gly Lys Thr
210                 215                 220

Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Glu Lys Lys Asp
            260                 265                 270

Phe Ala Ser Ile Leu Thr Asn Ala Ser Pro Leu Ala Val Asn Leu Leu
        275                 280                 285

Glu Lys Met Leu Val Leu Asp Ala Glu Gln Arg Val Thr Ala Gly Glu

```
                    290                 295                 300
Ala Leu Ala His Pro Tyr Phe Glu Ser Leu His Asp Thr Glu Asp Glu
305                 310                 315                 320

Pro Gln Val Gln Lys Tyr Asp Asp Ser Phe Asp Val Asp Arg Thr
                325                 330                 335

Leu Asp Glu Trp Lys Arg Val Thr Tyr Lys Glu Val Leu Ser Phe Lys
            340                 345                 350

Pro Pro Arg Gln Leu Gly Ala Arg Val Ser Lys Glu Thr Pro Leu
                355                 360                 365

<210> SEQ ID NO 18
<211> LENGTH: 469
<212> TYPE: PRT
<213> ORGANISM: Homo sapiens

<400> SEQUENCE: 18

Met His Ser Phe Pro Pro Leu Leu Leu Leu Phe Trp Gly Val Val
1               5                   10                  15

Ser His Ser Phe Pro Ala Thr Leu Glu Thr Gln Glu Gln Asp Val Asp
                20                  25                  30

Leu Val Gln Lys Tyr Leu Glu Lys Tyr Tyr Asn Leu Lys Asn Asp Gly
            35                  40                  45

Arg Gln Val Glu Lys Arg Arg Asn Ser Gly Pro Val Val Glu Lys Leu
50                  55                  60

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
                85                  90                  95

Val Ala Gln Phe Val Leu Thr Glu Gly Asn Pro Arg Trp Glu Gln Thr
            100                 105                 110

His Leu Thr Tyr Arg Ile Glu Asn Tyr Thr Pro Asp Leu Pro Arg Ala
            115                 120                 125

Asp Val Asp His Ala Ile Glu Lys Ala Phe Gln Leu Trp Ser Asn Val
            130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
            180                 185                 190

Gly Asp Ala His Phe Asp Glu Asp Glu Arg Trp Thr Asn Asn Phe Arg
            195                 200                 205

Glu Tyr Asn Leu His Arg Val Ala Ala His Glu Leu Gly His Ser Leu
            210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
                245                 250                 255

Gln Ala Ile Tyr Gly Arg Ser Gln Asn Pro Val Gln Pro Ile Gly Pro
            260                 265                 270

Gln Thr Pro Lys Ala Cys Asp Ser Lys Leu Thr Phe Asp Ala Ile Thr
            275                 280                 285

Thr Ile Arg Gly Glu Val Met Phe Phe Lys Asp Arg Phe Tyr Met Arg
            290                 295                 300
```

```
Thr Asn Pro Phe Tyr Pro Glu Val Glu Leu Asn Phe Ile Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
            340                 345                 350

Gly Gln Asn Val Leu His Gly Tyr Pro Lys Asp Ile Tyr Ser Ser Phe
                355                 360                 365

Gly Phe Pro Arg Thr Val Lys His Ile Asp Ala Ala Leu Ser Glu Glu
            370                 375                 380

Asn Thr Gly Lys Thr Tyr Phe Phe Val Ala Asn Lys Tyr Trp Arg Tyr
385                 390                 395                 400

Asp Glu Tyr Lys Arg Ser Met Asp Pro Gly Tyr Pro Lys Met Ile Ala
                405                 410                 415

His Asp Phe Pro Gly Ile Gly His Lys Val Asp Ala Val Phe Met Lys
            420                 425                 430

Asp Gly Phe Phe Tyr Phe Phe His Gly Thr Arg Gln Tyr Lys Phe Asp
                435                 440                 445

Pro Lys Thr Lys Arg Ile Leu Thr Leu Gln Lys Ala Asn Ser Trp Phe
            450                 455                 460

Asn Cys Arg Lys Asn
465

<210> SEQ ID NO 19
<211> LENGTH: 267
<212> TYPE: PRT
<213> ORGANISM: Homo sapiens

<400> SEQUENCE: 19

Met Arg Leu Thr Val Leu Cys Ala Val Cys Leu Leu Pro Gly Ser Leu
1               5                   10                  15

Ala Leu Pro Leu Pro Gln Glu Ala Gly Gly Met Ser Glu Leu Gln Trp
                20                  25                  30

Glu Gln Ala Gln Asp Tyr Leu Lys Arg Phe Tyr Leu Tyr Asp Ser Glu
            35                  40                  45

Thr Lys Asn Ala Asn Ser Leu Glu Ala Lys Leu Lys Glu Met Gln Lys
50                  55                  60

Phe Phe Gly Leu Pro Ile Thr Gly Met Leu Asn Ser Arg Val Ile Glu
65                  70                  75                  80

Ile Met Gln Lys Pro Arg Cys Gly Val Pro Asp Val Ala Glu Tyr Ser
                85                  90                  95

Leu Phe Pro Asn Ser Pro Lys Trp Thr Ser Lys Val Val Thr Tyr Arg
            100                 105                 110

Ile Val Ser Tyr Thr Arg Asp Leu Pro His Ile Thr Val Asp Arg Leu
        115                 120                 125

Val Ser Lys Ala Leu Asn Met Trp Gly Lys Glu Ile Pro Leu His Phe
    130                 135                 140

Arg Lys Val Val Trp Gly Thr Ala Asp Ile Met Ile Gly Phe Ala Arg
145                 150                 155                 160

Gly Ala His Gly Asp Ser Tyr Pro Phe Asp Gly Pro Gly Asn Thr Leu
                165                 170                 175

Ala His Ala Phe Ala Pro Gly Thr Gly Leu Gly Gly Asp Ala His Phe
            180                 185                 190

Asp Glu Asp Glu Arg Trp Thr Asp Gly Ser Ser Leu Gly Ile Asn Phe
        195                 200                 205
```

```
Leu Tyr Ala Ala Thr His Glu Leu Gly His Ser Leu Gly Met Gly His
        210                 215                 220

Ser Ser Asp Pro Asn Ala Val Met Tyr Pro Thr Tyr Gly Asn Gly Asp
225                 230                 235                 240

Pro Gln Asn Phe Lys Leu Ser Gln Asp Asp Ile Lys Gly Ile Gln Lys
                245                 250                 255

Leu Tyr Gly Lys Arg Ser Asn Ser Arg Lys Lys
        260                 265

<210> SEQ ID NO 20
<211> LENGTH: 5703
<212> TYPE: PRT
<213> ORGANISM: Homo sapiens

<400> SEQUENCE: 20

Met Gly Ala Pro Ser Ala Cys Arg Thr Leu Val Leu Ala Leu Ala Ala
1               5                   10                  15

Met Leu Val Val Pro Gln Ala Glu Thr Gln Gly Pro Val Glu Pro Ser
                20                  25                  30

Trp Gly Asn Ala Gly His Thr Met Asp Gly Gly Ala Pro Thr Ser Ser
            35                  40                  45

Pro Thr Arg Arg Val Ser Phe Val Pro Pro Val Thr Val Phe Pro Ser
    50                  55                  60

Leu Ser Pro Leu Asn Pro Ala His Asn Gly Arg Val Cys Ser Thr Trp
65                  70                  75                  80

Gly Asp Phe His Tyr Lys Thr Phe Asp Gly Asp Val Phe Arg Phe Pro
                85                  90                  95

Gly Leu Cys Asn Tyr Val Phe Ser Glu His Cys Arg Ala Ala Tyr Glu
            100                 105                 110

Asp Phe Asn Val Gln Leu Arg Arg Gly Leu Val Gly Ser Arg Pro Val
        115                 120                 125

Val Thr Arg Val Val Ile Lys Ala Gln Gly Leu Val Leu Glu Ala Ser
    130                 135                 140

Asn Gly Ser Val Leu Ile Asn Gly Gln Arg Glu Glu Leu Pro Tyr Ser
145                 150                 155                 160

Arg Thr Gly Leu Leu Val Glu Gln Ser Gly Asp Tyr Ile Lys Val Ser
                165                 170                 175

Ile Arg Leu Val Leu Thr Phe Leu Trp Asn Gly Glu Asp Ser Ala Leu
            180                 185                 190

Leu Glu Leu Asp Pro Lys Tyr Ala Asn Gln Thr Cys Gly Leu Cys Gly
        195                 200                 205

Asp Phe Asn Gly Leu Pro Ala Phe Asn Glu Phe Tyr Ala His Asn Ala
    210                 215                 220

Arg Leu Thr Pro Leu Gln Phe Gly Asn Leu Gln Lys Leu Asp Gly Pro
225                 230                 235                 240

Thr Glu Gln Cys Pro Asp Pro Leu Pro Leu Pro Ala Gly Asn Cys Thr
                245                 250                 255

Asp Glu Glu Gly Ile Cys His Arg Thr Leu Leu Gly Pro Ala Phe Ala
            260                 265                 270

Glu Cys His Ala Leu Val Asp Ser Thr Ala Tyr Leu Ala Ala Cys Ala
        275                 280                 285

Gln Asp Leu Cys Arg Cys Pro Thr Cys Pro Cys Ala Thr Phe Val Glu
    290                 295                 300

Tyr Ser Arg Gln Cys Ala His Ala Gly Gly Gln Pro Arg Asn Trp Arg
```

```
              305                 310                 315                 320
Cys Pro Glu Leu Cys Pro Arg Thr Cys Pro Leu Asn Met Gln His Gln
                325                 330                 335
Glu Cys Gly Ser Pro Cys Thr Asp Thr Cys Ser Asn Pro Gln Arg Ala
                340                 345                 350
Gln Leu Cys Glu Asp His Cys Val Asp Gly Cys Phe Cys Pro Pro Gly
                355                 360                 365
Ser Thr Val Leu Asp Asp Ile Thr His Ser Gly Cys Leu Pro Leu Gly
        370                 375                 380
Gln Cys Pro Cys Thr His Gly Gly Arg Thr Tyr Ser Pro Gly Thr Ser
385                 390                 395                 400
Phe Asn Thr Thr Cys Ser Ser Cys Thr Cys Ser Gly Gly Leu Trp Gln
                    405                 410                 415
Cys Gln Asp Leu Pro Cys Pro Gly Thr Cys Ser Val Gln Gly Gly Ala
                420                 425                 430
His Ile Ser Thr Tyr Asp Glu Lys Leu Tyr Asp Leu His Gly Asp Cys
            435                 440                 445
Ser Tyr Val Leu Ser Lys Lys Cys Ala Asp Ser Ser Phe Thr Val Leu
        450                 455                 460
Ala Glu Leu Arg Lys Cys Gly Leu Thr Asp Asn Glu Asn Cys Leu Lys
465                 470                 475                 480
Ala Val Thr Leu Ser Leu Asp Gly Gly Asp Thr Ala Ile Arg Val Gln
                485                 490                 495
Ala Asp Gly Gly Val Phe Leu Asn Ser Ile Tyr Thr Gln Leu Pro Leu
                500                 505                 510
Ser Ala Ala Asn Ile Thr Leu Phe Thr Pro Ser Ser Phe Phe Ile Val
            515                 520                 525
Val Gln Thr Gly Leu Gly Leu Gln Leu Leu Val Gln Leu Val Pro Leu
        530                 535                 540
Met Gln Val Phe Val Arg Leu Asp Pro Ala His Gln Gly Gln Met Cys
545                 550                 555                 560
Gly Leu Cys Gly Asn Phe Asn Gln Asn Gln Ala Asp Asp Phe Thr Ala
                    565                 570                 575
Leu Ser Gly Val Val Glu Ala Thr Gly Ala Ala Phe Ala Asn Thr Trp
                580                 585                 590
Lys Ala Gln Ala Ala Cys Ala Asn Ala Arg Asn Ser Phe Glu Asp Pro
            595                 600                 605
Cys Ser Leu Ser Val Glu Asn Glu Asn Tyr Ala Arg His Trp Cys Ser
        610                 615                 620
Arg Leu Thr Asp Pro Asn Ser Ala Phe Ser Arg Cys His Ser Ile Ile
625                 630                 635                 640
Asn Pro Lys Pro Phe His Ser Asn Cys Met Phe Asp Thr Cys Asn Cys
                    645                 650                 655
Glu Arg Ser Glu Asp Cys Leu Cys Ala Ala Leu Ser Ser Tyr Val His
                660                 665                 670
Ala Cys Ala Ala Lys Gly Val Gln Leu Ser Asp Trp Arg Asp Gly Val
            675                 680                 685
Cys Thr Lys Tyr Met Gln Asn Cys Pro Lys Ser Gln Arg Tyr Ala Tyr
        690                 695                 700
Val Val Asp Ala Cys Gln Pro Thr Cys Arg Gly Leu Ser Glu Ala Asp
705                 710                 715                 720
Val Thr Cys Ser Val Ser Phe Val Pro Val Asp Gly Cys Thr Cys Pro
                    725                 730                 735
```

-continued

```
Ala Gly Thr Phe Leu Asn Asp Ala Gly Ala Cys Val Pro Ala Gln Glu
            740                 745                 750

Cys Pro Cys Tyr Ala His Gly Thr Val Leu Ala Pro Gly Glu Val Val
            755                 760                 765

His Asp Glu Gly Ala Val Cys Ser Cys Thr Gly Gly Lys Leu Ser Cys
770                 775                 780

Leu Gly Ala Ser Leu Gln Lys Ser Thr Gly Cys Ala Ala Pro Met Val
785                 790                 795                 800

Tyr Leu Asp Cys Ser Asn Ser Ser Ala Gly Thr Pro Gly Ala Glu Cys
            805                 810                 815

Leu Arg Ser Cys His Thr Leu Asp Val Gly Cys Phe Ser Thr His Cys
            820                 825                 830

Val Ser Gly Cys Val Cys Pro Pro Gly Leu Val Ser Asp Gly Ser Gly
            835                 840                 845

Gly Cys Ile Ala Glu Glu Asp Cys Pro Cys Val His Asn Glu Ala Thr
            850                 855                 860

Tyr Lys Pro Gly Glu Thr Ile Arg Val Asp Cys Asn Thr Cys Thr Cys
865                 870                 875                 880

Arg Asn Arg Arg Trp Glu Cys Ser His Arg Leu Cys Leu Gly Thr Cys
            885                 890                 895

Val Ala Tyr Gly Asp Gly His Phe Ile Thr Phe Asp Gly Asp Arg Tyr
            900                 905                 910

Ser Phe Glu Gly Ser Cys Glu Tyr Ile Leu Ala Gln Asp Tyr Cys Gly
            915                 920                 925

Asp Asn Thr Thr His Gly Thr Phe Arg Ile Val Thr Glu Asn Ile Pro
930                 935                 940

Cys Gly Thr Thr Gly Thr Thr Cys Ser Lys Ala Ile Lys Leu Phe Val
945                 950                 955                 960

Glu Ser Tyr Glu Leu Ile Leu Gln Gly Gly Thr Phe Lys Ala Val Ala
            965                 970                 975

Arg Gly Pro Gly Gly Asp Pro Pro Tyr Lys Ile Arg Tyr Met Gly Ile
            980                 985                 990

Phe Leu Val Ile Glu Thr His Gly Met Ala Val Ser Trp Asp Arg Lys
            995                 1000                1005

Thr Ser Val Phe Ile Arg Leu His Gln Asp Tyr Lys Gly Arg Val
    1010                1015                1020

Cys Gly Leu Cys Gly Asn Phe Asp Asp Asn Ala Ile Asn Asp Phe
    1025                1030                1035

Ala Thr Arg Ser Arg Ser Val Val Gly Asp Ala Leu Glu Phe Gly
    1040                1045                1050

Asn Ser Trp Lys Leu Ser Pro Ser Cys Pro Asp Ala Leu Ala Pro
    1055                1060                1065

Lys Asp Pro Cys Thr Ala Asn Pro Phe Arg Lys Ser Trp Ala Gln
    1070                1075                1080

Lys Gln Cys Ser Ile Leu His Gly Pro Thr Phe Ala Ala Cys Arg
    1085                1090                1095

Ser Gln Val Asp Ser Thr Lys Tyr Tyr Glu Ala Cys Val Asn Asp
    1100                1105                1110

Ala Cys Ala Cys Asp Ser Gly Gly Asp Cys Glu Cys Phe Cys Thr
    1115                1120                1125

Ala Val Ala Ala Tyr Ala Gln Ala Cys His Asp Ala Gly Leu Cys
    1130                1135                1140
```

-continued

Val Ser Trp Arg Thr Pro Asp Thr Cys Pro Leu Phe Cys Asp Phe
1145                 1150                 1155

Tyr Asn Pro His Gly Gly Cys Glu Trp His Tyr Gln Pro Cys Gly
1160                 1165                 1170

Ala Pro Cys Leu Lys Thr Cys Arg Asn Pro Ser Gly His Cys Leu
1175                 1180                 1185

Val Asp Leu Pro Gly Leu Glu Gly Cys Tyr Pro Lys Cys Pro Pro
1190                 1195                 1200

Ser Gln Pro Phe Phe Asn Glu Asp Gln Met Lys Cys Val Ala Gln
1205                 1210                 1215

Cys Gly Cys Tyr Asp Lys Asp Gly Asn Tyr Tyr Asp Val Gly Ala
1220                 1225                 1230

Arg Val Pro Thr Ala Glu Asn Cys Gln Ser Cys Asn Cys Thr Pro
1235                 1240                 1245

Ser Gly Ile Gln Cys Ala His Ser Leu Glu Ala Cys Thr Cys Thr
1250                 1255                 1260

Tyr Glu Asp Arg Thr Tyr Ser Tyr Gln Asp Val Ile Tyr Asn Thr
1265                 1270                 1275

Thr Asp Gly Leu Gly Ala Cys Leu Ile Ala Ile Cys Gly Ser Asn
1280                 1285                 1290

Gly Thr Ile Ile Arg Lys Ala Val Ala Cys Pro Gly Thr Pro Ala
1295                 1300                 1305

Thr Thr Pro Phe Thr Phe Thr Thr Ala Trp Val Pro His Ser Thr
1310                 1315                 1320

Thr Ser Pro Ala Leu Pro Val Ser Thr Val Cys Val Arg Glu Val
1325                 1330                 1335

Cys Arg Trp Ser Ser Trp Tyr Asn Gly His Arg Pro Glu Pro Gly
1340                 1345                 1350

Leu Gly Gly Gly Asp Phe Glu Thr Phe Glu Asn Leu Arg Gln Arg
1355                 1360                 1365

Gly Tyr Gln Val Cys Pro Val Leu Ala Asp Ile Glu Cys Arg Ala
1370                 1375                 1380

Ala Gln Leu Pro Asp Met Pro Leu Glu Glu Leu Gly Gln Gln Val
1385                 1390                 1395

Asp Cys Asp Arg Met Arg Gly Leu Met Cys Ala Asn Ser Gln Gln
1400                 1405                 1410

Ser Pro Pro Leu Cys His Asp Tyr Glu Leu Arg Val Leu Cys Cys
1415                 1420                 1425

Glu Tyr Val Pro Cys Gly Pro Ser Pro Ala Pro Gly Thr Ser Pro
1430                 1435                 1440

Gln Pro Ser Leu Ser Ala Ser Thr Glu Pro Ala Val Pro Thr Pro
1445                 1450                 1455

Thr Gln Thr Thr Ala Thr Glu Lys Thr Thr Leu Trp Val Thr Pro
1460                 1465                 1470

Ser Ile Arg Ser Thr Ala Ala Leu Thr Ser Gln Thr Gly Ser Ser
1475                 1480                 1485

Ser Gly Pro Val Thr Val Thr Pro Ser Ala Pro Gly Thr Thr Thr
1490                 1495                 1500

Cys Gln Pro Arg Cys Gln Trp Thr Glu Trp Phe Asp Glu Asp Tyr
1505                 1510                 1515

Pro Lys Ser Glu Gln Leu Gly Gly Asp Val Glu Ser Tyr Asp Lys
1520                 1525                 1530

Ile Arg Ala Ala Gly Gly His Leu Cys Gln Gln Pro Lys Asp Ile

-continued

```
            1535                1540                1545
Glu Cys Gln Ala Glu Ser Phe Pro Asn Trp Thr Leu Ala Gln Val
    1550                1555                1560
Gly Gln Lys Val His Cys Asp Val His Phe Gly Leu Val Cys Arg
    1565                1570                1575
Asn Trp Glu Gln Glu Gly Val Phe Lys Met Cys Tyr Asn Tyr Arg
    1580                1585                1590
Ile Arg Val Leu Cys Cys Ser Asp Asp His Cys Arg Gly Arg Ala
    1595                1600                1605
Thr Thr Pro Pro Pro Thr Thr Glu Leu Glu Thr Ala Thr Thr Thr
    1610                1615                1620
Thr Thr Gln Ala Leu Phe Ser Thr Pro Gln Pro Thr Ser Ser Pro
    1625                1630                1635
Gly Leu Thr Arg Ala Pro Pro Ala Ser Thr Thr Ala Val Pro Thr
    1640                1645                1650
Leu Ser Glu Gly Leu Thr Ser Pro Arg Tyr Thr Ser Thr Leu Gly
    1655                1660                1665
Thr Ala Thr Thr Gly Gly Pro Arg Gln Ser Ala Gly Ser Thr Glu
    1670                1675                1680
Pro Thr Val Pro Gly Val Ala Thr Ser Thr Leu Pro Thr Arg Ser
    1685                1690                1695
Ala Leu Pro Gly Thr Thr Gly Ser Leu Gly Thr Trp Arg Pro Ser
    1700                1705                1710
Gln Pro Pro Thr Leu Ala Pro Thr Thr Met Ala Thr Ser Arg Ala
    1715                1720                1725
Arg Pro Thr Gly Thr Ala Ser Thr Ala Ser Lys Glu Pro Leu Thr
    1730                1735                1740
Thr Ser Leu Ala Pro Thr Leu Thr Ser Glu Leu Ser Thr Ser Gln
    1745                1750                1755
Ala Glu Thr Ser Thr Pro Arg Thr Glu Thr Thr Met Ser Pro Leu
    1760                1765                1770
Thr Asn Thr Thr Thr Ser Gln Gly Thr Thr Arg Cys Gln Pro Lys
    1775                1780                1785
Cys Glu Trp Thr Glu Trp Phe Asp Val Asp Phe Pro Thr Ser Gly
    1790                1795                1800
Val Ala Ser Gly Asp Met Glu Thr Phe Glu Asn Ile Arg Ala Ala
    1805                1810                1815
Gly Gly Lys Met Cys Trp Ala Pro Lys Ser Ile Glu Cys Arg Ala
    1820                1825                1830
Glu Asn Tyr Pro Glu Val Ser Ile Asp Gln Val Gly Gln Val Leu
    1835                1840                1845
Thr Cys Ser Leu Glu Thr Gly Leu Thr Cys Lys Asn Glu Asp Gln
    1850                1855                1860
Thr Gly Arg Phe Asn Met Cys Phe Asn Tyr Asn Val Arg Val Leu
    1865                1870                1875
Cys Cys Asp Asp Tyr Ser His Cys Pro Ser Thr Leu Ala Thr Ser
    1880                1885                1890
Ser Thr Ala Thr Pro Ser Ser Thr Pro Gly Thr Thr Trp Ile Leu
    1895                1900                1905
Thr Lys Pro Thr Thr Thr Ala Thr Thr Thr Ala Ser Thr Gly Ser
    1910                1915                1920
Thr Ala Thr Ala Ser Ser Thr Gln Ala Thr Ala Gly Thr Pro His
    1925                1930                1935
```

```
Val Ser Thr Thr Ala Thr Thr Pro Thr Val Thr Ser Ser Lys Ala
    1940            1945             1950

Thr Pro Phe Ser Ser Pro Gly Thr Ala Thr Ala Leu Pro Ala Leu
    1955            1960             1965

Arg Ser Thr Ala Thr Thr Pro Thr Ala Thr Ser Phe Thr Ala Ile
    1970            1975             1980

Pro Ser Ser Ser Leu Gly Thr Thr Trp Thr Arg Leu Ser Gln Thr
    1985            1990             1995

Thr Thr Pro Met Ala Thr Met Ser Thr Ala Thr Pro Ser Ser Thr
    2000            2005             2010

Pro Glu Thr Val His Thr Ser Thr Val Leu Thr Thr Thr Ala Thr
    2015            2020             2025

Thr Thr Gly Ala Thr Gly Ser Val Ala Thr Pro Ser Ser Thr Pro
    2030            2035             2040

Gly Thr Ala His Thr Thr Lys Val Leu Thr Thr Thr Thr Thr Gly
    2045            2050             2055

Phe Thr Ala Thr Pro Ser Ser Ser Pro Gly Arg Ala Arg Thr Leu
    2060            2065             2070

Pro Val Trp Ile Ser Thr Thr Thr Thr Pro Thr Thr Arg Gly Ser
    2075            2080             2085

Thr Val Thr Pro Ser Ser Ile Pro Gly Thr Thr His Thr Pro Thr
    2090            2095             2100

Val Leu Thr Thr Thr Thr Thr Val Ala Thr Gly Ser Met Ala
    2105            2110             2115

Thr Pro Ser Ser Ser Thr Gln Thr Ser Gly Thr Pro Pro Ser Leu
    2120            2125             2130

Thr Thr Thr Ala Thr Thr Ile Thr Ala Thr Gly Ser Thr Thr Asn
    2135            2140             2145

Pro Ser Ser Thr Pro Gly Thr Pro Ile Pro Pro Val Leu Thr
    2150            2155             2160

Thr Thr Ala Thr Thr Pro Ala Ala Thr Ser Ser Thr Val Thr Pro
    2165            2170             2175

Ser Ser Ala Leu Gly Thr Thr His Thr Pro Pro Val Pro Asn Thr
    2180            2185             2190

Thr Ala Thr Thr His Gly Arg Ser Leu Ser Pro Ser Ser Pro His
    2195            2200             2205

Thr Val Cys Thr Ala Trp Thr Ala Thr Ser Gly Ile Leu Gly
    2210            2215             2220

Thr Thr His Ile Thr Glu Pro Ser Thr Gly Thr Ser His Thr Pro
    2225            2230             2235

Ala Ala Thr Thr Gly Thr Thr Gln His Ser Thr Pro Ala Leu Ser
    2240            2245             2250

Ser Pro His Pro Ser Ser Arg Thr Thr Glu Ser Pro Pro Ser Pro
    2255            2260             2265

Gly Thr Thr Thr Pro Gly His Thr Thr Ala Thr Ser Arg Thr Thr
    2270            2275             2280

Ala Thr Ala Thr Pro Ser Lys Thr Arg Thr Ser Thr Leu Leu Pro
    2285            2290             2295

Ser Gln Pro Thr Ser Ala Pro Ile Thr Thr Val Val Thr Met Gly
    2300            2305             2310

Cys Glu Pro Gln Cys Ala Trp Ser Glu Trp Leu Asp Tyr Ser Tyr
    2315            2320             2325
```

```
Pro Met Pro Gly Pro Ser Gly Gly Asp Phe Asp Thr Tyr Ser Asn
    2330            2335            2340

Ile Arg Ala Ala Gly Gly Ala Val Cys Glu Gln Pro Leu Gly Leu
    2345            2350            2355

Glu Cys Arg Ala Gln Ala Gln Pro Gly Val Pro Leu Arg Glu Leu
    2360            2365            2370

Gly Gln Val Val Glu Cys Ser Leu Asp Phe Gly Leu Val Cys Arg
    2375            2380            2385

Asn Arg Glu Gln Val Gly Lys Phe Lys Met Cys Phe Asn Tyr Glu
    2390            2395            2400

Ile Arg Val Phe Cys Cys Asn Tyr Gly His Cys Pro Ser Thr Pro
    2405            2410            2415

Ala Thr Ser Ser Thr Ala Thr Pro Ser Ser Thr Pro Gly Thr Thr
    2420            2425            2430

Trp Ile Leu Thr Glu Leu Thr Thr Thr Ala Thr Thr Thr Glu Ser
    2435            2440            2445

Thr Gly Ser Thr Ala Thr Pro Thr Ser Thr Leu Arg Thr Ala Pro
    2450            2455            2460

Pro Pro Lys Val Leu Thr Thr Thr Ala Thr Thr Pro Thr Val Thr
    2465            2470            2475

Ser Ser Lys Ala Thr Pro Ser Ser Ser Pro Gly Thr Ala Thr Ala
    2480            2485            2490

Leu Pro Ala Leu Arg Ser Thr Ala Thr Thr Pro Thr Ala Thr Ser
    2495            2500            2505

Val Thr Pro Ile Pro Ser Ser Ser Leu Gly Thr Thr Trp Thr Arg
    2510            2515            2520

Leu Ser Gln Thr Thr Thr Pro Thr Ala Thr Met Ser Thr Ala Thr
    2525            2530            2535

Pro Ser Ser Thr Pro Glu Thr Ala His Thr Ser Thr Val Leu Thr
    2540            2545            2550

Ala Thr Ala Thr Thr Thr Gly Ala Thr Gly Ser Val Ala Thr Pro
    2555            2560            2565

Ser Ser Thr Pro Gly Thr Ala His Thr Thr Lys Val Pro Thr Thr
    2570            2575            2580

Thr Thr Thr Gly Phe Thr Ala Thr Pro Ser Ser Ser Pro Gly Thr
    2585            2590            2595

Ala Leu Thr Pro Pro Val Trp Ile Ser Thr Thr Thr Thr Pro Thr
    2600            2605            2610

Thr Arg Gly Ser Thr Val Thr Pro Ser Ser Ile Pro Gly Thr Thr
    2615            2620            2625

His Thr Ala Thr Val Leu Thr Thr Thr Thr Thr Val Ala Thr
    2630            2635            2640

Gly Ser Met Ala Thr Pro Ser Ser Ser Thr Gln Thr Ser Gly Thr
    2645            2650            2655

Pro Pro Ser Leu Thr Thr Thr Ala Thr Thr Ile Thr Ala Thr Gly
    2660            2665            2670

Ser Thr Thr Asn Pro Ser Ser Thr Pro Gly Thr Arg Pro Ile Pro
    2675            2680            2685

Pro Val Leu Thr Thr Thr Ala Thr Thr Pro Ala Ala Thr Ser Ser
    2690            2695            2700

Thr Val Thr Pro Ser Ser Ala Leu Gly Thr Thr His Thr Pro Pro
    2705            2710            2715

Val Pro Asn Thr Thr Ala Thr Thr His Gly Arg Ser Leu Ser Pro
```

-continued

```
            2720                2725                2730
Ser Ser Pro His Thr Val Arg Thr Ala Trp Thr Ser Ala Thr Ser
        2735                2740                2745
Gly Thr Leu Gly Thr Thr His Ile Thr Glu Pro Ser Thr Gly Thr
        2750                2755                2760
Ser His Thr Pro Ala Ala Thr Thr Gly Thr Thr Gln His Ser Thr
        2765                2770                2775
Pro Ala Leu Ser Ser Pro His Pro Ser Ser Arg Thr Thr Glu Ser
        2780                2785                2790
Pro Pro Ser Pro Gly Thr Thr Thr Pro Gly His Thr Thr Ala Thr
        2795                2800                2805
Ser Arg Thr Thr Ala Thr Ala Thr Pro Ser Lys Thr Arg Thr Ser
        2810                2815                2820
Thr Leu Leu Pro Ser Ser Pro Thr Ser Ala Pro Ile Thr Thr Val
        2825                2830                2835
Val Thr Met Gly Cys Glu Pro Gln Cys Ala Trp Ser Glu Trp Leu
        2840                2845                2850
Asp Tyr Ser Tyr Pro Met Pro Gly Pro Ser Gly Gly Asp Phe Asp
        2855                2860                2865
Thr Tyr Ser Asn Ile Arg Ala Ala Gly Gly Ala Val Cys Glu Gln
        2870                2875                2880
Pro Leu Gly Leu Glu Cys Arg Ala Gln Ala Gln Pro Gly Val Pro
        2885                2890                2895
Leu Arg Glu Leu Gly Gln Val Val Glu Cys Ser Leu Asp Phe Gly
        2900                2905                2910
Leu Val Cys Arg Asn Arg Glu Gln Val Gly Lys Phe Lys Met Cys
        2915                2920                2925
Phe Asn Tyr Glu Ile Arg Val Phe Cys Cys Asn Tyr Gly His Cys
        2930                2935                2940
Pro Ser Thr Pro Ala Thr Ser Ser Thr Ala Thr Pro Ser Ser Thr
        2945                2950                2955
Pro Gly Thr Thr Trp Ile Leu Thr Glu Gln Thr Thr Ala Ala Thr
        2960                2965                2970
Thr Thr Ala Thr Thr Gly Ser Thr Ala Ile Pro Ser Ser Thr Pro
        2975                2980                2985
Gly Thr Ala Pro Pro Lys Val Leu Thr Ser Gln Ala Thr Thr
        2990                2995                3000
Pro Thr Ala Thr Ser Ser Lys Ala Thr Ser Ser Ser Pro Arg
        3005                3010                3015
Thr Ala Thr Thr Leu Pro Val Leu Thr Ser Thr Ala Thr Lys Ser
        3020                3025                3030
Thr Ala Thr Ser Phe Thr Pro Ile Pro Ser Ser Thr Leu Gly Thr
        3035                3040                3045
Thr Gly Thr Ser Gln Asn Arg Pro Pro His Pro Met Ala Thr Met
        3050                3055                3060
Ser Thr Ile His Pro Ser Ser Thr Pro Glu Thr Thr His Thr Ser
        3065                3070                3075
Thr Val Leu Thr Thr Lys Ala Thr Thr Thr Arg Ala Thr Ser Ser
        3080                3085                3090
Met Ser Thr Pro Ser Ser Thr Pro Gly Thr Thr Trp Ile Leu Thr
        3095                3100                3105
Glu Leu Thr Thr Ala Ala Thr Thr Ala Ala Leu Pro His Gly
        3110                3115                3120
```

-continued

```
Thr Pro Ser Ser Thr Pro Gly Thr Thr Trp Ile Leu Thr Glu Pro
    3125                3130                3135
Ser Thr Thr Ala Thr Val Thr Val Pro Thr Gly Ser Thr Ala Thr
    3140                3145                3150
Ala Ser Ser Thr Arg Ala Thr Ala Gly Thr Leu Lys Val Leu Thr
    3155                3160                3165
Ser Thr Ala Thr Thr Pro Val Ile Ser Ser Arg Ala Thr Pro
    3170                3175                3180
Ser Ser Ser Pro Gly Thr Ala Thr Ala Leu Pro Ala Leu Arg Ser
    3185                3190                3195
Thr Ala Thr Thr Pro Thr Ala Thr Ser Val Thr Ala Ile Pro Ser
    3200                3205                3210
Ser Ser Leu Gly Thr Ala Trp Thr Arg Leu Ser Gln Thr Thr Thr
    3215                3220                3225
Pro Thr Ala Thr Met Ser Thr Ala Thr Pro Ser Ser Thr Pro Glu
    3230                3235                3240
Thr Val His Thr Ser Thr Val Leu Thr Thr Thr Ala Thr Thr Thr
    3245                3250                3255
Arg Thr Gly Ser Val Ala Thr Pro Ser Ser Thr Pro Gly Thr Ala
    3260                3265                3270
His Thr Thr Lys Val Pro Thr Thr Thr Thr Thr Gly Phe Thr Ala
    3275                3280                3285
Thr Pro Ser Ser Ser Pro Gly Thr Ala Leu Thr Pro Pro Val Trp
    3290                3295                3300
Ile Ser Thr Thr Thr Thr Pro Thr Thr Arg Gly Ser Thr Val Thr
    3305                3310                3315
Pro Ser Ser Ile Pro Gly Thr Thr His Thr Ala Thr Val Leu Thr
    3320                3325                3330
Thr Thr Thr Thr Thr Val Ala Thr Gly Ser Met Ala Thr Pro Ser
    3335                3340                3345
Ser Ser Thr Gln Thr Ser Gly Thr Pro Pro Ser Leu Thr Thr Thr
    3350                3355                3360
Ala Thr Thr Ile Thr Ala Thr Gly Ser Thr Thr Asn Pro Ser Ser
    3365                3370                3375
Thr Pro Gly Thr Thr Pro Ile Pro Pro Val Leu Thr Thr Thr Ala
    3380                3385                3390
Thr Thr Pro Ala Ala Thr Ser Ser Thr Val Thr Pro Ser Ser Ala
    3395                3400                3405
Leu Gly Thr Thr His Thr Pro Pro Val Pro Asn Thr Thr Ala Thr
    3410                3415                3420
Thr His Gly Arg Ser Leu Pro Pro Ser Ser Pro His Thr Val Pro
    3425                3430                3435
Thr Ala Trp Thr Ser Ala Thr Ser Gly Ile Leu Gly Thr Thr His
    3440                3445                3450
Ile Thr Glu Pro Ser Thr Gly Thr Ser His Thr Pro Ala Ala Thr
    3455                3460                3465
Thr Gly Thr Thr Gln Pro Ser Thr Pro Ala Leu Ser Ser Pro His
    3470                3475                3480
Pro Ser Ser Arg Thr Thr Glu Ser Pro Pro Ser Pro Gly Thr Thr
    3485                3490                3495
Thr Pro Gly His Thr Arg Gly Thr Ser Arg Thr Thr Ala Thr Ala
    3500                3505                3510
```

-continued

Thr Pro Ser Lys Thr Arg Thr Ser Thr Leu Leu Pro Ser Ser Pro
3515              3520                3525

Thr Ser Ala Pro Ile Thr Val Val Thr Thr Gly Cys Glu Pro
3530              3535                3540

Gln Cys Ala Trp Ser Glu Trp Leu Asp Tyr Ser Tyr Pro Met Pro
3545              3550                3555

Gly Pro Ser Gly Gly Asp Phe Asp Thr Tyr Ser Asn Ile Arg Ala
3560              3565                3570

Ala Gly Gly Ala Val Cys Glu Gln Pro Leu Gly Leu Glu Cys Arg
3575              3580                3585

Ala Gln Ala Gln Pro Gly Val Pro Leu Arg Glu Leu Gly Gln Val
3590              3595                3600

Val Glu Cys Ser Leu Asp Phe Gly Leu Val Cys Arg Asn Arg Glu
3605              3610                3615

Gln Val Gly Lys Phe Lys Met Cys Phe Asn Tyr Glu Ile Arg Val
3620              3625                3630

Phe Cys Cys Asn Tyr Gly His Cys Pro Ser Thr Pro Ala Thr Ser
3635              3640                3645

Ser Thr Ala Thr Pro Ser Ser Thr Pro Gly Thr Thr Trp Ile Leu
3650              3655                3660

Thr Lys Leu Thr Thr Thr Ala Thr Thr Thr Glu Ser Thr Gly Ser
3665              3670                3675

Thr Ala Thr Pro Ser Ser Thr Gln Gly Pro Pro Ala Gly Thr Pro
3680              3685                3690

His Val Ser Thr Thr Ala Thr Thr Pro Thr Val Thr Ser Ser Lys
3695              3700                3705

Ala Thr Pro Phe Ser Ser Pro Gly Thr Ala Thr Ala Leu Pro Ala
3710              3715                3720

Leu Arg Ser Thr Ala Thr Thr Pro Thr Ala Thr Ser Phe Thr Ala
3725              3730                3735

Ile Pro Ser Ser Ser Leu Gly Thr Thr Trp Thr Arg Leu Ser Gln
3740              3745                3750

Thr Thr Thr Pro Met Ala Thr Met Ser Thr Ala Thr Pro Ser Ser
3755              3760                3765

Thr Pro Glu Thr Val His Thr Ser Thr Val Leu Thr Thr Thr Ala
3770              3775                3780

Thr Thr Thr Gly Ala Thr Gly Ser Val Ala Thr Pro Ser Ser Thr
3785              3790                3795

Pro Gly Thr Ala His Thr Thr Lys Val Pro Thr Thr Thr Thr Thr
3800              3805                3810

Gly Phe Thr Val Thr Pro Ser Ser Ser Pro Gly Thr Ala Arg Thr
3815              3820                3825

Pro Pro Val Trp Ile Ser Thr Thr Thr Thr Pro Thr Thr Ser Gly
3830              3835                3840

Ser Thr Val Thr Pro Ser Ser Ile Pro Gly Thr Thr His Thr Pro
3845              3850                3855

Thr Val Leu Thr Thr Thr Thr Gln Pro Val Ala Thr Gly Ser Met
3860              3865                3870

Ala Thr Pro Ser Ser Ser Thr Gln Thr Ser Gly Thr Pro Pro Ser
3875              3880                3885

Leu Ile Thr Thr Ala Thr Thr Ile Thr Ala Thr Gly Ser Thr Thr
3890              3895                3900

Asn Pro Ser Ser Thr Pro Gly Thr Thr Pro Ile Pro Pro Glu Leu

```
                    3905                3910                3915
Thr Thr Thr Ala Thr Thr Pro Ala Ala Thr Ser Ser Thr Val Thr
    3920            3925                3930

Pro Ser Ser Ala Leu Gly Thr Thr His Thr Pro Val Pro Asn
3935                3940                3945

Thr Thr Ala Thr Thr His Gly Arg Ser Leu Ser Pro Ser Ser Pro
    3950            3955                3960

His Thr Val Arg Thr Ala Trp Thr Ser Ala Thr Ser Gly Thr Leu
3965                3970                3975

Gly Thr Thr His Ile Thr Glu Pro Ser Thr Gly Thr Ser His Thr
    3980            3985                3990

Pro Ala Ala Thr Thr Gly Thr Thr Thr Ser Thr Pro Ala Leu
3995                4000                4005

Ser Ser Pro His Pro Ser Ser Arg Thr Thr Glu Ser Pro Pro Ser
    4010            4015                4020

Pro Gly Thr Thr Thr Pro Gly His Thr Thr Ala Thr Ser Arg Thr
4025                4030                4035

Thr Ala Thr Ala Thr Pro Ser Lys Thr Arg Thr Ser Thr Leu Leu
    4040            4045                4050

Pro Ser Gln Pro Thr Ser Ala Pro Ile Thr Thr Val Val Thr Thr
4055                4060                4065

Gly Cys Glu Pro Gln Cys Ala Trp Ser Glu Trp Leu Asp Tyr Ser
    4070            4075                4080

Tyr Pro Met Pro Gly Pro Ser Gly Gly Asp Phe Asp Thr Tyr Ser
4085                4090                4095

Asn Ile Arg Ala Ala Gly Gly Ala Val Cys Glu Gln Pro Leu Gly
    4100            4105                4110

Leu Glu Cys Arg Ala Gln Ala Gln Pro Gly Val Pro Leu Gly Glu
4115                4120                4125

Leu Gly Gln Val Val Glu Cys Ser Leu Asp Phe Gly Leu Val Cys
    4130            4135                4140

Arg Asn Arg Glu Gln Val Gly Lys Phe Lys Met Cys Phe Asn Tyr
4145                4150                4155

Glu Ile Arg Val Phe Cys Cys Asn Tyr Gly His Cys Pro Ser Thr
    4160            4165                4170

Pro Ala Thr Ser Ser Thr Ala Met Pro Ser Ser Thr Pro Gly Thr
4175                4180                4185

Thr Trp Ile Leu Thr Glu Leu Thr Thr Thr Ala Thr Thr Thr Ala
    4190            4195                4200

Ser Thr Gly Ser Thr Ala Thr Pro Ser Ser Thr Pro Gly Thr Ala
4205                4210                4215

Pro Pro Pro Lys Val Leu Thr Ser Pro Ala Thr Thr Pro Thr Ala
    4220            4225                4230

Thr Ser Ser Lys Ala Thr Ser Ser Ser Ser Pro Arg Thr Ala Thr
4235                4240                4245

Thr Leu Pro Val Leu Thr Ser Thr Ala Thr Lys Ser Thr Ala Thr
    4250            4255                4260

Ser Val Thr Pro Ile Pro Ser Ser Thr Leu Gly Thr Thr Gly Thr
4265                4270                4275

Leu Pro Glu Gln Thr Thr Thr Pro Val Ala Thr Met Ser Thr Ile
    4280            4285                4290

His Pro Ser Ser Thr Pro Glu Thr Thr His Thr Ser Thr Val Leu
4295                4300                4305
```

-continued

Thr Thr Lys Ala Thr Thr Arg Ala Thr Ser Thr Ser Thr Pro
4310            4315            4320

Ser Ser Thr Pro Gly Thr Thr Trp Ile Leu Thr Glu Leu Thr Thr
4325            4330            4335

Ala Ala Thr Thr Thr Ala Gly Thr Gly Pro Thr Ala Thr Pro Ser
4340            4345            4350

Ser Thr Pro Gly Thr Thr Trp Ile Leu Thr Glu Leu Thr Thr Thr
4355            4360            4365

Ala Thr Thr Thr Ala Ser Thr Gly Ser Thr Ala Thr Leu Ser Ser
4370            4375            4380

Thr Pro Gly Thr Thr Trp Ile Leu Thr Glu Pro Ser Thr Thr Ala
4385            4390            4395

Thr Val Thr Val Pro Thr Gly Ser Thr Ala Thr Ala Ser Ser Thr
4400            4405            4410

Gln Ala Thr Ala Gly Thr Pro His Val Ser Thr Thr Ala Thr Thr
4415            4420            4425

Pro Thr Val Thr Ser Ser Lys Ala Thr Pro Ser Ser Ser Pro Gly
4430            4435            4440

Thr Ala Thr Ala Leu Pro Ala Leu Arg Ser Thr Ala Thr Thr Pro
4445            4450            4455

Thr Ala Thr Ser Phe Thr Ala Ile Pro Ser Ser Ser Leu Gly Thr
4460            4465            4470

Thr Trp Thr Arg Leu Ser Gln Thr Thr Thr Pro Thr Ala Thr Met
4475            4480            4485

Ser Thr Ala Thr Pro Ser Ser Thr Pro Glu Thr Val His Thr Ser
4490            4495            4500

Thr Val Leu Thr Thr Thr Ala Thr Thr Thr Gly Ala Thr Gly Ser
4505            4510            4515

Val Ala Thr Pro Ser Ser Thr Pro Gly Thr Ala His Thr Thr Lys
4520            4525            4530

Val Pro Thr Thr Thr Thr Thr Gly Phe Thr Ala Thr Pro Ser Ser
4535            4540            4545

Ser Pro Gly Thr Ala Leu Thr Pro Pro Val Trp Ile Ser Thr Thr
4550            4555            4560

Thr Thr Pro Thr Thr Thr Thr Pro Thr Thr Ser Gly Ser Thr Val
4565            4570            4575

Thr Pro Ser Ser Ile Pro Gly Thr Thr His Thr Ala Arg Val Leu
4580            4585            4590

Thr Thr Thr Thr Thr Val Ala Thr Gly Ser Met Ala Thr Pro
4595            4600            4605

Ser Ser Ser Thr Gln Thr Ser Gly Thr Pro Pro Ser Leu Thr Thr
4610            4615            4620

Thr Ala Thr Thr Ile Thr Ala Thr Gly Ser Thr Thr Asn Pro Ser
4625            4630            4635

Ser Thr Pro Gly Thr Thr Pro Ile Pro Pro Val Leu Thr Ser Met
4640            4645            4650

Ala Thr Thr Pro Ala Ala Thr Ser Ser Lys Ala Thr Ser Ser Ser
4655            4660            4665

Ser Pro Arg Thr Ala Thr Thr Leu Pro Val Leu Thr Ser Thr Ala
4670            4675            4680

Thr Lys Ser Thr Ala Thr Ser Phe Thr Pro Ile Pro Ser Ser Thr
4685            4690            4695

```
Leu Trp Thr Thr Trp Thr Val Pro Ala Gln Thr Thr Thr Pro Met
    4700            4705                4710

Ser Thr Met Ser Thr Ile His Thr Ser Ser Thr Pro Glu Thr Thr
    4715            4720                4725

His Thr Ser Thr Val Leu Thr Thr Thr Ala Thr Met Thr Arg Ala
    4730            4735                4740

Thr Asn Ser Thr Ala Thr Pro Ser Ser Thr Leu Gly Thr Thr Arg
    4745            4750                4755

Ile Leu Thr Glu Leu Thr Thr Thr Ala Thr Thr Thr Ala Ala Thr
    4760            4765                4770

Gly Ser Thr Ala Thr Leu Ser Ser Thr Pro Gly Thr Thr Trp Ile
    4775            4780                4785

Leu Thr Glu Pro Ser Thr Ile Ala Thr Val Met Val Pro Thr Gly
    4790            4795                4800

Ser Thr Ala Thr Thr Ser Ser Thr Leu Gly Thr Ala His Thr Pro
    4805            4810                4815

Lys Val Val Thr Ala Met Ala Thr Met Pro Thr Ala Thr Ala Ser
    4820            4825                4830

Thr Val Pro Ser Ser Ser Thr Val Gly Thr Thr Arg Thr Pro Ala
    4835            4840                4845

Val Leu Pro Ser Ser Leu Pro Thr Phe Ser Val Ser Thr Val Ser
    4850            4855                4860

Ser Ser Val Leu Thr Thr Leu Arg Pro Thr Gly Phe Pro Ser Ser
    4865            4870                4875

His Phe Ser Thr Pro Cys Phe Cys Arg Ala Phe Gly Gln Phe Phe
    4880            4885                4890

Ser Pro Gly Glu Val Ile Tyr Asn Lys Thr Asp Arg Ala Gly Cys
    4895            4900                4905

His Phe Tyr Ala Val Cys Asn Gln His Cys Asp Ile Asp Arg Phe
    4910            4915                4920

Gln Gly Ala Cys Pro Thr Ser Pro Pro Val Ser Ser Ala Pro
    4925            4930                4935

Leu Ser Ser Pro Ser Pro Ala Pro Gly Cys Asp Asn Ala Ile Pro
    4940            4945                4950

Leu Arg Gln Val Asn Glu Thr Trp Thr Leu Glu Asn Cys Thr Val
    4955            4960                4965

Ala Arg Cys Val Gly Asp Asn Arg Val Val Leu Leu Asp Pro Lys
    4970            4975                4980

Pro Val Ala Asn Val Thr Cys Val Asn Lys His Leu Pro Ile Lys
    4985            4990                4995

Val Ser Asp Pro Ser Gln Pro Cys Asp Phe His Tyr Glu Cys Glu
    5000            5005                5010

Cys Ile Cys Ser Met Trp Gly Gly Ser His Tyr Ser Thr Phe Asp
    5015            5020                5025

Gly Thr Ser Tyr Thr Phe Arg Gly Asn Cys Thr Tyr Val Leu Met
    5030            5035                5040

Arg Glu Ile His Ala Arg Phe Gly Asn Leu Ser Leu Tyr Leu Asp
    5045            5050                5055

Asn His Tyr Cys Thr Ala Ser Ala Thr Ala Ala Ala Ala Arg Cys
    5060            5065                5070

Pro Arg Ala Leu Ser Ile His Tyr Lys Ser Met Asp Ile Val Leu
    5075            5080                5085

Thr Val Thr Met Val His Gly Lys Glu Glu Gly Leu Ile Leu Phe
```

-continued

```
         5090                5095                5100
Asp Gln Ile Pro Val Ser Ser Gly Phe Ser Lys Asn Gly Val Leu
    5105                5110                5115
Val Ser Val Leu Gly Thr Thr Thr Met Arg Val Asp Ile Pro Ala
    5120                5125                5130
Leu Gly Val Thr Val Thr Phe Asn Gly Gln Val Phe Gln Ala Arg
    5135                5140                5145
Leu Pro Tyr Ser Leu Phe His Asn Asn Thr Glu Gly Gln Cys Gly
    5150                5155                5160
Thr Cys Thr Asn Asn Gln Arg Asp Asp Cys Leu Gln Arg Asp Gly
    5165                5170                5175
Thr Thr Ala Ala Ser Cys Lys Asp Met Ala Lys Thr Trp Leu Val
    5180                5185                5190
Pro Asp Ser Arg Lys Asp Gly Cys Trp Ala Pro Thr Gly Thr Pro
    5195                5200                5205
Pro Thr Ala Ser Pro Ala Ala Pro Val Ser Ser Thr Pro Thr Pro
    5210                5215                5220
Thr Pro Cys Pro Pro Gln Pro Leu Cys Asp Leu Met Leu Ser Gln
    5225                5230                5235
Val Phe Ala Glu Cys His Asn Leu Val Pro Pro Gly Pro Phe Phe
    5240                5245                5250
Asn Ala Cys Ile Ser Asp His Cys Arg Gly Arg Leu Glu Val Pro
    5255                5260                5265
Cys Gln Ser Leu Glu Ala Tyr Ala Glu Leu Cys Arg Ala Arg Gly
    5270                5275                5280
Val Cys Ser Asp Trp Arg Gly Ala Thr Gly Gly Leu Cys Asp Leu
    5285                5290                5295
Thr Cys Pro Pro Thr Lys Val Tyr Lys Pro Cys Gly Pro Ile Gln
    5300                5305                5310
Pro Ala Thr Cys Asn Ser Arg Asn Gln Ser Pro Gln Leu Glu Gly
    5315                5320                5325
Met Ala Glu Gly Cys Phe Cys Pro Glu Asp Gln Ile Leu Phe Asn
    5330                5335                5340
Ala His Met Gly Ile Cys Val Gln Ala Cys Pro Cys Val Gly Pro
    5345                5350                5355
Asp Gly Phe Pro Lys Phe Pro Gly Glu Arg Trp Val Ser Asn Cys
    5360                5365                5370
Gln Ser Cys Val Cys Asp Glu Gly Ser Val Ser Val Gln Cys Lys
    5375                5380                5385
Pro Leu Pro Cys Asp Ala Gln Gly Gln Pro Pro Cys Asn Arg
    5390                5395                5400
Pro Gly Phe Val Thr Val Thr Arg Pro Arg Ala Glu Asn Pro Cys
    5405                5410                5415
Cys Pro Glu Thr Val Cys Val Cys Asn Thr Thr Thr Cys Pro Gln
    5420                5425                5430
Ser Leu Pro Val Cys Pro Pro Gly Gln Glu Ser Ile Cys Thr Gln
    5435                5440                5445
Glu Glu Gly Asp Cys Cys Pro Thr Phe Arg Cys Arg Pro Gln Leu
    5450                5455                5460
Cys Ser Tyr Asn Gly Thr Phe Tyr Gly Val Gly Ala Thr Phe Pro
    5465                5470                5475
Gly Ala Leu Pro Cys His Met Cys Thr Cys Leu Ser Gly Asp Thr
    5480                5485                5490
```

-continued

Gln Asp Pro Thr Val Gln Cys Gln Glu Asp Ala Cys Asn Asn Thr
    5495                5500                5505

Thr Cys Pro Gln Gly Phe Glu Tyr Lys Arg Val Ala Gly Gln Cys
    5510                5515                5520

Cys Gly Glu Cys Val Gln Thr Ala Cys Leu Thr Pro Asp Gly Gln
    5525                5530                5535

Pro Val Gln Leu Asn Glu Thr Trp Val Asn Ser His Val Asp Asn
    5540                5545                5550

Cys Thr Val Tyr Leu Cys Glu Ala Glu Gly Gly Val His Leu Leu
    5555                5560                5565

Thr Pro Gln Pro Ala Ser Cys Pro Asp Val Ser Ser Cys Arg Gly
    5570                5575                5580

Ser Leu Arg Lys Thr Gly Cys Cys Tyr Ser Cys Glu Glu Asp Ser
    5585                5590                5595

Cys Gln Val Arg Ile Asn Thr Thr Ile Leu Trp His Gln Gly Cys
    5600                5605                5610

Glu Thr Glu Val Asn Ile Thr Phe Cys Glu Gly Ser Cys Pro Gly
    5615                5620                5625

Ala Ser Lys Tyr Ser Ala Glu Ala Gln Ala Met Gln His Gln Cys
    5630                5635                5640

Thr Cys Cys Gln Glu Arg Arg Val His Glu Glu Thr Val Pro Leu
    5645                5650                5655

His Cys Pro Asn Gly Ser Ala Ile Leu His Thr Tyr Thr His Val
    5660                5665                5670

Asp Glu Cys Gly Cys Thr Pro Phe Cys Val Pro Ala Pro Met Ala
    5675                5680                5685

Pro Pro His Thr Arg Gly Phe Pro Ala Gln Glu Ala Thr Ala Val
    5690                5695                5700

<210> SEQ ID NO 21
<211> LENGTH: 344
<212> TYPE: PRT
<213> ORGANISM: Homo sapiens

<400> SEQUENCE: 21

Met Ser Gly Glu Pro Glu Leu Ile Glu Leu Arg Glu Leu Ala Pro Ala
1               5                   10                  15

Gly Arg Ala Gly Lys Gly Arg Thr Arg Leu Glu Arg Ala Asn Ala Leu
            20                  25                  30

Arg Ile Ala Arg Gly Thr Ala Cys Asn Pro Thr Arg Gln Leu Val Pro
        35                  40                  45

Gly Arg Gly His Arg Phe Gln Pro Ala Gly Pro Ala Thr His Thr Trp
    50                  55                  60

Cys Asp Leu Cys Gly Asp Phe Ile Trp Gly Val Val Arg Lys Gly Leu
65                  70                  75                  80

Gln Cys Ala Arg Leu Ser Ala Asp Cys Lys Phe Thr Cys His Tyr Arg
                85                  90                  95

Cys Arg Ala Leu Val Cys Leu Asp Cys Cys Gly Pro Arg Asp Leu Gly
            100                 105                 110

Trp Glu Pro Ala Val Glu Arg Asp Thr Asn Val Asp Glu Pro Val Glu
        115                 120                 125

Trp Glu Thr Pro Asp Leu Ser Gln Ala Glu Ile Glu Gln Lys Ile Lys
    130                 135                 140

Glu Tyr Asn Ala Gln Ile Asn Ser Asn Leu Phe Met Ser Leu Asn Lys

```
                145                 150                 155                 160
Asp Gly Ser Tyr Thr Gly Phe Ile Lys Val Gln Leu Lys Leu Val Arg
                165                 170                 175
Pro Val Ser Val Pro Ser Ser Lys Lys Pro Ser Leu Gln Asp Ala
            180                 185                 190
Arg Arg Gly Pro Gly Arg Gly Thr Ser Val Arg Arg Thr Ser Phe
        195                 200                 205
Tyr Leu Pro Lys Asp Ala Val Lys His Leu His Val Leu Ser Arg Thr
    210                 215                 220
Arg Ala Arg Glu Val Ile Glu Ala Leu Leu Arg Lys Phe Leu Val Val
225                 230                 235                 240
Asp Asp Pro Arg Lys Phe Ala Leu Phe Glu Arg Ala Glu Arg His Gly
                245                 250                 255
Gln Val Tyr Leu Arg Lys Leu Leu Asp Asp Glu Gln Pro Leu Arg Leu
            260                 265                 270
Arg Leu Leu Ala Gly Pro Ser Asp Lys Ala Leu Ser Phe Val Leu Lys
        275                 280                 285
Glu Asn Asp Ser Gly Glu Val Asn Trp Asp Ala Phe Ser Met Pro Glu
    290                 295                 300
Leu His Asn Phe Leu Arg Ile Leu Gln Arg Glu Glu Glu His Leu
305                 310                 315                 320
Arg Gln Ile Leu Gln Lys Tyr Ser Tyr Cys Arg Gln Lys Ile Gln Glu
                325                 330                 335
Ala Leu His Ala Cys Pro Leu Gly
            340

<210> SEQ ID NO 22
<211> LENGTH: 90
<212> TYPE: PRT
<213> ORGANISM: Homo sapiens

<400> SEQUENCE: 22

Met Ala Cys Pro Leu Asp Gln Ala Ile Gly Leu Leu Val Ala Ile Phe
1               5                   10                  15
His Lys Tyr Ser Gly Arg Glu Gly Asp Lys His Thr Leu Ser Lys Lys
                20                  25                  30
Glu Leu Lys Glu Leu Ile Gln Lys Glu Leu Thr Ile Gly Ser Lys Leu
            35                  40                  45
Gln Asp Ala Glu Ile Ala Arg Leu Met Glu Asp Leu Asp Arg Asn Lys
        50                  55                  60
Asp Gln Glu Val Asn Phe Gln Glu Tyr Val Thr Phe Leu Gly Ala Leu
65                  70                  75                  80
Ala Leu Ile Tyr Asn Glu Ala Leu Lys Gly
                85                  90

<210> SEQ ID NO 23
<211> LENGTH: 2214
<212> TYPE: PRT
<213> ORGANISM: Homo sapiens

<400> SEQUENCE: 23

Met Ala Thr Arg Ser Ser Arg Arg Glu Ser Arg Leu Pro Phe Leu Phe
1               5                   10                  15
Thr Leu Val Ala Leu Leu Pro Pro Gly Ala Leu Cys Glu Val Trp Thr
                20                  25                  30
Gln Arg Leu His Gly Gly Ser Ala Pro Leu Pro Gln Asp Arg Gly Phe
```

```
            35                  40                  45
Leu Val Val Gln Gly Asp Pro Arg Glu Leu Arg Leu Trp Ala Arg Gly
 50                  55                  60

Asp Ala Arg Gly Ala Ser Arg Ala Asp Glu Lys Pro Leu Arg Arg Lys
 65                  70                  75                  80

Arg Ser Ala Ala Leu Gln Pro Glu Pro Ile Lys Val Tyr Gly Gln Val
                     85                  90                  95

Ser Leu Asn Asp Ser His Asn Gln Met Val Val His Trp Ala Gly Glu
                100                 105                 110

Lys Ser Asn Val Ile Val Ala Leu Ala Arg Asp Ser Leu Ala Leu Ala
                115                 120                 125

Arg Pro Lys Ser Ser Asp Val Tyr Val Ser Tyr Asp Tyr Gly Lys Ser
                130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
                180                 185                 190

Phe Cys Asn Thr Leu Gln Gly Phe Ser Ile Pro Phe Arg Ala Ala Asp
                195                 200                 205

Leu Leu Leu His Ser Lys Ala Ser Asn Leu Leu Gly Phe Asp Arg
                210                 215                 220

Ser His Pro Asn Lys Gln Leu Trp Lys Ser Asp Asp Phe Gly Gln Thr
225                 230                 235                 240

Trp Ile Met Ile Gln Glu His Val Lys Ser Phe Ser Trp Gly Ile Asp
                    245                 250                 255

Pro Tyr Asp Lys Pro Asn Thr Ile Tyr Ile Glu Arg His Glu Pro Ser
                260                 265                 270

Gly Tyr Ser Thr Val Phe Arg Ser Thr Asp Phe Phe Gln Ser Arg Glu
                275                 280                 285

Asn Gln Glu Val Ile Leu Glu Glu Val Arg Asp Phe Gln Leu Arg Asp
290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                325                 330                 335

Ala Ala Gln Phe Val Thr Arg His Pro Ile Asn Glu Tyr Tyr Ile Ala
                340                 345                 350

Asp Ala Ser Glu Asp Gln Val Phe Val Cys Val Ser His Ser Asn Asn
                355                 360                 365

Arg Thr Asn Leu Tyr Ile Ser Glu Ala Glu Gly Leu Lys Phe Ser Leu
                370                 375                 380

Ser Leu Glu Asn Val Leu Tyr Tyr Ser Pro Gly Gly Ala Gly Ser Asp
385                 390                 395                 400

Thr Leu Val Arg Tyr Phe Ala Asn Glu Pro Phe Ala Asp Phe His Arg
                    405                 410                 415

Val Glu Gly Leu Gln Gly Val Tyr Ile Ala Thr Leu Ile Asn Gly Ser
                420                 425                 430

Met Asn Glu Glu Asn Met Arg Ser Val Ile Thr Phe Asp Lys Gly Gly
                435                 440                 445

Thr Trp Glu Phe Leu Gln Ala Pro Ala Phe Thr Gly Tyr Gly Glu Lys
                450                 455                 460
```

```
Ile Asn Cys Glu Leu Ser Gln Gly Cys Ser Leu His Leu Ala Gln Arg
465                 470                 475                 480

Leu Ser Gln Leu Leu Asn Leu Gln Leu Arg Arg Met Pro Ile Leu Ser
                485                 490                 495

Lys Glu Ser Ala Pro Gly Leu Ile Ile Ala Thr Gly Ser Val Gly Lys
            500                 505                 510

Asn Leu Ala Ser Lys Thr Asn Val Tyr Ile Ser Ser Ala Gly Ala
            515                 520                 525

Arg Trp Arg Glu Ala Leu Pro Gly Pro His Tyr Tyr Thr Trp Gly Asp
            530                 535                 540

His Gly Gly Ile Ile Thr Ala Ile Ala Gln Gly Met Glu Thr Asn Glu
545                 550                 555                 560

Leu Lys Tyr Ser Thr Asn Glu Gly Glu Thr Trp Lys Thr Phe Ile Phe
                565                 570                 575

Ser Glu Lys Pro Val Phe Val Tyr Gly Leu Leu Thr Glu Pro Gly Glu
            580                 585                 590

Lys Ser Thr Val Phe Thr Ile Phe Gly Ser Asn Lys Glu Asn Val His
            595                 600                 605

Ser Trp Leu Ile Leu Gln Val Asn Ala Thr Asp Ala Leu Gly Val Pro
610                 615                 620

Cys Thr Glu Asn Asp Tyr Lys Leu Trp Ser Pro Ser Asp Glu Arg Gly
625                 630                 635                 640

Asn Glu Cys Leu Leu Gly His Lys Thr Val Phe Lys Arg Arg Thr Pro
                645                 650                 655

His Ala Thr Cys Phe Asn Gly Glu Asp Phe Asp Arg Pro Val Val Val
            660                 665                 670

Ser Asn Cys Ser Cys Thr Arg Glu Asp Tyr Glu Cys Asp Phe Gly Phe
            675                 680                 685

Lys Met Ser Glu Asp Leu Ser Leu Glu Val Cys Val Pro Asp Pro Glu
690                 695                 700

Phe Ser Gly Lys Ser Tyr Ser Pro Val Pro Cys Pro Val Gly Ser
705                 710                 715                 720

Thr Tyr Arg Arg Thr Arg Gly Tyr Arg Lys Ile Ser Gly Asp Thr Cys
                725                 730                 735

Ser Gly Gly Asp Val Glu Ala Arg Leu Glu Gly Glu Leu Val Pro Cys
            740                 745                 750

Pro Leu Ala Glu Glu Asn Glu Phe Ile Leu Tyr Ala Val Arg Lys Ser
            755                 760                 765

Ile Tyr Arg Tyr Asp Leu Ala Ser Gly Ala Thr Glu Gln Leu Pro Leu
            770                 775                 780

Thr Gly Leu Arg Ala Ala Val Ala Leu Asp Phe Asp Tyr Glu His Asn
785                 790                 795                 800

Cys Leu Tyr Trp Ser Asp Leu Ala Leu Asp Val Ile Gln Arg Leu Cys
                805                 810                 815

Leu Asn Gly Ser Thr Gly Gln Glu Val Ile Ile Asn Ser Gly Leu Glu
            820                 825                 830

Thr Val Glu Ala Leu Ala Phe Glu Pro Leu Ser Gln Leu Leu Tyr Trp
            835                 840                 845

Val Asp Ala Gly Phe Lys Lys Ile Glu Val Ala Asn Pro Asp Gly Asp
            850                 855                 860

Phe Arg Leu Thr Ile Val Asn Ser Ser Val Leu Asp Arg Pro Arg Ala
865                 870                 875                 880
```

```
Leu Val Leu Val Pro Gln Glu Gly Val Met Phe Trp Thr Asp Trp Gly
                885                 890                 895

Asp Leu Lys Pro Gly Ile Tyr Arg Ser Asn Met Asp Gly Ser Ala Ala
            900                 905                 910

Tyr His Leu Val Ser Glu Asp Val Lys Trp Pro Asn Gly Ile Ser Val
        915                 920                 925

Asp Asp Gln Trp Ile Tyr Trp Thr Asp Ala Tyr Leu Glu Cys Ile Glu
930                 935                 940

Arg Ile Thr Phe Ser Gly Gln Gln Arg Ser Val Ile Leu Asp Asn Leu
945                 950                 955                 960

Pro His Pro Tyr Ala Ile Ala Val Phe Lys Asn Glu Ile Tyr Trp Asp
            965                 970                 975

Asp Trp Ser Gln Leu Ser Ile Phe Arg Ala Ser Lys Tyr Ser Gly Ser
        980                 985                 990

Gln Met Glu Ile Leu Ala Asn Gln Leu Thr Gly Leu Met Asp Met Lys
    995                 1000                1005

Ile Phe Tyr Lys Gly Lys Asn Thr Gly Ser Asn Ala Cys Val Pro
    1010                1015                1020

Arg Pro Cys Ser Leu Leu Cys Leu Pro Lys Ala Asn Asn Ser Arg
    1025                1030                1035

Ser Cys Arg Cys Pro Glu Asp Val Ser Ser Val Leu Pro Ser
    1040                1045                1050

Gly Asp Leu Met Cys Asp Cys Pro Gln Gly Tyr Gln Leu Lys Asn
    1055                1060                1065

Asn Thr Cys Val Lys Gln Glu Asn Thr Cys Leu Arg Asn Gln Tyr
    1070                1075                1080

Arg Cys Ser Asn Gly Asn Cys Ile Asn Ser Ile Trp Trp Cys Asp
    1085                1090                1095

Phe Asp Asn Asp Cys Gly Asp Met Ser Asp Glu Arg Asn Cys Pro
    1100                1105                1110

Thr Thr Ile Cys Asp Leu Asp Thr Gln Phe Arg Cys Gln Glu Ser
    1115                1120                1125

Gly Thr Cys Ile Pro Leu Ser Tyr Lys Cys Asp Leu Glu Asp Asp
    1130                1135                1140

Cys Gly Asp Asn Ser Asp Glu Ser His Cys Glu Met His Gln Cys
    1145                1150                1155

Arg Ser Asp Glu Tyr Asn Cys Ser Ser Gly Met Cys Ile Arg Ser
    1160                1165                1170

Ser Trp Val Cys Asp Gly Asp Asn Asp Cys Arg Asp Trp Ser Asp
    1175                1180                1185

Glu Ala Asn Cys Thr Ala Ile Tyr His Thr Cys Glu Ala Ser Asn
    1190                1195                1200

Phe Gln Cys Arg Asn Gly His Cys Ile Pro Gln Arg Trp Ala Cys
    1205                1210                1215

Asp Gly Asp Thr Asp Cys Gln Asp Gly Ser Asp Glu Asp Pro Val
    1220                1225                1230

Asn Cys Glu Lys Lys Cys Asn Gly Phe Arg Cys Pro Asn Gly Thr
    1235                1240                1245

Cys Ile Pro Ser Ser Lys His Cys Asp Gly Leu Arg Asp Cys Ser
    1250                1255                1260

Asp Gly Ser Asp Glu Gln His Cys Glu Pro Leu Cys Thr His Phe
    1265                1270                1275

Met Asp Phe Val Cys Lys Asn Arg Gln Gln Cys Leu Phe His Ser
```

```
            1280                1285                1290
Met Val Cys Asp Gly Ile Ile Gln Cys Arg Asp Gly Ser Asp Glu
        1295                1300                1305

Asp Ala Ala Phe Ala Gly Cys Ser Gln Asp Pro Glu Phe His Lys
        1310                1315                1320

Val Cys Asp Glu Phe Gly Phe Gln Cys Gln Asn Gly Val Cys Ile
        1325                1330                1335

Ser Leu Ile Trp Lys Cys Asp Gly Met Asp Asp Cys Gly Asp Tyr
        1340                1345                1350

Ser Asp Glu Ala Asn Cys Glu Asn Pro Thr Glu Ala Pro Asn Cys
        1355                1360                1365

Ser Arg Tyr Phe Gln Phe Arg Cys Glu Asn Gly His Cys Ile Pro
        1370                1375                1380

Asn Arg Trp Lys Cys Asp Arg Glu Asn Asp Cys Gly Asp Trp Ser
        1385                1390                1395

Asp Glu Lys Asp Cys Gly Asp Ser His Ile Leu Pro Phe Ser Thr
        1400                1405                1410

Pro Gly Pro Ser Thr Cys Leu Pro Asn Tyr Tyr Arg Cys Ser Ser
        1415                1420                1425

Gly Thr Cys Val Met Asp Thr Trp Val Cys Asp Gly Tyr Arg Asp
        1430                1435                1440

Cys Ala Asp Gly Ser Asp Glu Glu Ala Cys Pro Leu Leu Ala Asn
        1445                1450                1455

Val Thr Ala Ala Ser Thr Pro Thr Gln Leu Gly Arg Cys Asp Arg
        1460                1465                1470

Phe Glu Phe Glu Cys His Gln Pro Lys Thr Cys Ile Pro Asn Trp
        1475                1480                1485

Lys Arg Cys Asp Gly His Gln Asp Cys Gln Asp Gly Arg Asp Glu
        1490                1495                1500

Ala Asn Cys Pro Thr His Ser Thr Leu Thr Cys Met Ser Arg Glu
        1505                1510                1515

Phe Gln Cys Glu Asp Gly Glu Ala Cys Ile Val Leu Ser Glu Arg
        1520                1525                1530

Cys Asp Gly Phe Leu Asp Cys Ser Asp Glu Ser Asp Glu Lys Ala
        1535                1540                1545

Cys Ser Asp Glu Leu Thr Val Tyr Lys Val Gln Asn Leu Gln Trp
        1550                1555                1560

Thr Ala Asp Phe Ser Gly Asp Val Thr Leu Thr Trp Met Arg Pro
        1565                1570                1575

Lys Lys Met Pro Ser Ala Ser Cys Val Tyr Asn Val Tyr Tyr Arg
        1580                1585                1590

Val Val Gly Glu Ser Ile Trp Lys Thr Leu Glu Thr His Ser Asn
        1595                1600                1605

Lys Thr Asn Thr Val Leu Lys Val Leu Lys Pro Asp Thr Thr Tyr
        1610                1615                1620

Gln Val Lys Val Gln Val Gln Cys Leu Ser Lys Ala His Asn Thr
        1625                1630                1635

Asn Asp Phe Val Thr Leu Arg Thr Pro Glu Gly Leu Pro Asp Ala
        1640                1645                1650

Pro Arg Asn Leu Gln Leu Ser Leu Pro Arg Glu Ala Glu Gly Val
        1655                1660                1665

Ile Val Gly His Trp Ala Pro Pro Ile His Thr His Gly Leu Ile
        1670                1675                1680
```

-continued

Arg Glu Tyr Ile Val Glu Tyr Ser Arg Ser Gly Ser Lys Met Trp
1685                1690                1695

Ala Ser Gln Arg Ala Ala Ser Asn Phe Thr Glu Ile Lys Asn Leu
1700                1705                1710

Leu Val Asn Thr Leu Tyr Thr Val Arg Val Ala Ala Val Thr Ser
1715                1720                1725

Arg Gly Ile Gly Asn Trp Ser Asp Ser Lys Ser Ile Thr Thr Ile
1730                1735                1740

Lys Gly Lys Val Ile Pro Pro Asp Ile His Ile Asp Ser Tyr
1745                1750                1755

Gly Glu Asn Tyr Leu Ser Phe Thr Leu Thr Met Glu Ser Asp Ile
1760                1765                1770

Lys Val Asn Gly Tyr Val Val Asn Leu Phe Trp Ala Phe Asp Thr
1775                1780                1785

His Lys Gln Glu Arg Arg Thr Leu Asn Phe Arg Gly Ser Ile Leu
1790                1795                1800

Ser His Lys Val Gly Asn Leu Thr Ala His Thr Ser Tyr Glu Ile
1805                1810                1815

Ser Ala Trp Ala Lys Thr Asp Leu Gly Asp Ser Pro Leu Ala Phe
1820                1825                1830

Glu His Val Met Thr Arg Gly Val Arg Pro Pro Ala Pro Ser Leu
1835                1840                1845

Lys Ala Lys Ala Ile Asn Gln Thr Ala Val Glu Cys Thr Trp Thr
1850                1855                1860

Gly Pro Arg Asn Val Val Tyr Gly Ile Phe Tyr Ala Thr Ser Phe
1865                1870                1875

Leu Asp Leu Tyr Arg Asn Pro Lys Ser Leu Thr Thr Ser Leu His
1880                1885                1890

Asn Lys Thr Val Ile Val Ser Lys Asp Glu Gln Tyr Leu Phe Leu
1895                1900                1905

Val Arg Val Val Val Pro Tyr Gln Gly Pro Ser Ser Asp Tyr Val
1910                1915                1920

Val Val Lys Met Ile Pro Asp Ser Arg Leu Pro Pro Arg His Leu
1925                1930                1935

His Val Val His Thr Gly Lys Thr Ser Val Val Ile Lys Trp Glu
1940                1945                1950

Ser Pro Tyr Asp Ser Pro Asp Gln Asp Leu Leu Tyr Ala Val Ala
1955                1960                1965

Val Lys Asp Leu Ile Arg Lys Thr Asp Arg Ser Tyr Lys Val Lys
1970                1975                1980

Ser Arg Asn Ser Thr Val Glu Tyr Thr Leu Asn Lys Leu Glu Pro
1985                1990                1995

Gly Gly Lys Tyr His Ile Ile Val Gln Leu Gly Asn Met Ser Lys
2000                2005                2010

Asp Ser Ser Ile Lys Ile Thr Thr Val Ser Leu Ser Ala Pro Asp
2015                2020                2025

Ala Leu Lys Ile Ile Thr Glu Asn Asp His Val Leu Leu Phe Trp
2030                2035                2040

Lys Ser Leu Ala Leu Lys Glu Lys His Phe Asn Glu Ser Arg Gly
2045                2050                2055

Tyr Glu Ile His Met Phe Asp Ser Ala Met Asn Ile Thr Ala Tyr
2060                2065                2070

```
Leu Gly Asn Thr Thr Asp Asn Phe Phe Lys Ile Ser Asn Leu Lys
    2075                2080                2085

Met Gly His Asn Tyr Thr Phe Thr Val Gln Ala Arg Cys Leu Phe
    2090                2095                2100

Gly Asn Gln Ile Cys Gly Glu Pro Ala Ile Leu Leu Tyr Asp Glu
    2105                2110                2115

Leu Gly Ser Gly Ala Asp Ala Ser Ala Thr Gln Ala Ala Arg Ser
    2120                2125                2130

Thr Asp Val Ala Ala Val Val Pro Ile Leu Phe Leu Ile Leu
    2135                2140                2145

Leu Ser Leu Gly Val Gly Phe Ala Ile Leu Tyr Thr Lys His Arg
    2150                2155                2160

Arg Leu Gln Ser Ser Phe Thr Ala Phe Ala Asn Ser His Tyr Ser
    2165                2170                2175

Ser Arg Leu Gly Ser Ala Ile Phe Ser Ser Gly Asp Asp Leu Gly
    2180                2185                2190

Glu Asp Asp Glu Asp Ala Pro Met Ile Thr Gly Phe Ser Asp Asp
    2195                2200                2205

Val Pro Met Val Ile Ala
    2210

<210> SEQ ID NO 24
<211> LENGTH: 222
<212> TYPE: PRT
<213> ORGANISM: Homo sapiens

<400> SEQUENCE: 24

Met Cys Leu Arg Leu Gly Gly Leu Ser Val Gly Asp Phe Arg Lys Val
1               5                   10                  15

Leu Met Lys Thr Gly Leu Val Leu Val Leu Gly His Val Ser Phe
                20                  25                  30

Ile Thr Ala Ala Leu Phe His Gly Thr Val Leu Arg Tyr Val Gly Thr
            35                  40                  45

Pro Gln Asp Ala Val Ala Leu Gln Tyr Cys Val Val Asn Ile Leu Ser
50                  55                  60

Val Thr Ser Ala Ile Val Ile Thr Ser Gly Ile Ala Ala Ile Val
65                  70                  75                  80

Leu Ser Arg Tyr Leu Pro Ser Thr Pro Leu Arg Trp Thr Val Phe Ser
                85                  90                  95

Ser Ser Val Ala Cys Ala Leu Leu Ser Leu Thr Cys Ala Leu Gly Leu
                100                 105                 110

Leu Ala Ser Ile Ala Met Thr Phe Ala Thr Gln Gly Lys Ala Leu Leu
            115                 120                 125

Ala Ala Cys Thr Phe Gly Ser Ser Glu Leu Leu Leu Ala Leu Ala Pro Asp
130                 135                 140

Cys Pro Phe Asp Pro Thr Arg Ile Tyr Ser Ser Ser Leu Cys Leu Trp
145                 150                 155                 160

Gly Ile Ala Leu Val Leu Cys Val Ala Glu Asn Val Phe Ala Val Arg
                165                 170                 175

Cys Ala Gln Leu Thr His Gln Leu Leu Glu Leu Arg Pro Trp Trp Gly
            180                 185                 190

Lys Ser Ser His His Met Met Arg Glu Asn Pro Glu Leu Val Glu Gly
        195                 200                 205

Arg Asp Leu Leu Ser Cys Thr Ser Ser Glu Pro Leu Thr Leu
210                 215                 220
```

<210> SEQ ID NO 25
<211> LENGTH: 335
<212> TYPE: PRT
<213> ORGANISM: Homo sapiens

<400> SEQUENCE: 25

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335
```

<210> SEQ ID NO 26
<211> LENGTH: 597
<212> TYPE: PRT
<213> ORGANISM: Homo sapiens

<400> SEQUENCE: 26

```
Met Glu Ala Glu Pro Pro Leu Tyr Pro Met Ala Gly Ala Ala Gly Pro
1               5                   10                  15

Gln Gly Asp Glu Asp Leu Leu Gly Val Pro Asp Gly Pro Glu Ala Pro
            20                  25                  30

Leu Asp Glu Leu Val Gly Ala Tyr Pro Asn Tyr Asn Glu Glu Glu Glu
        35                  40                  45

Glu Arg Arg Tyr Tyr Arg Arg Lys Arg Leu Gly Val Leu Lys Asn Val
    50                  55                  60

Leu Ala Ala Ser Ala Gly Gly Met Leu Thr Tyr Gly Val Tyr Leu Gly
65                  70                  75                  80

Leu Leu Gln Met Gln Leu Ile Leu His Tyr Asp Glu Thr Tyr Arg Glu
                85                  90                  95

Val Lys Tyr Gly Asn Met Gly Leu Pro Asp Ile Asp Ser Lys Met Leu
            100                 105                 110

Met Gly Ile Asn Val Thr Pro Ile Ala Ala Leu Leu Tyr Thr Pro Val
            115                 120                 125

Leu Ile Arg Phe Phe Gly Thr Lys Trp Met Met Phe Leu Ala Val Gly
    130                 135                 140

Ile Tyr Ala Leu Phe Val Ser Thr Asn Tyr Trp Glu Arg Tyr Tyr Thr
145                 150                 155                 160

Leu Val Pro Ser Ala Val Ala Leu Gly Met Ala Ile Val Pro Leu Trp
                165                 170                 175

Ala Ser Met Gly Asn Tyr Ile Thr Arg Met Ala Gln Lys Tyr His Glu
            180                 185                 190

Tyr Ser His Tyr Lys Glu Gln Asp Gly Gln Gly Met Lys Gln Arg Pro
            195                 200                 205

Pro Arg Gly Ser His Ala Pro Tyr Leu Leu Val Phe Gln Ala Ile Phe
    210                 215                 220

Tyr Ser Phe Phe His Leu Ser Phe Ala Cys Ala Gln Leu Pro Met Ile
225                 230                 235                 240

Tyr Phe Leu Asn His Tyr Leu Tyr Asp Leu Asn His Thr Leu Tyr Asn
                245                 250                 255

Val Gln Ser Cys Gly Thr Asn Ser His Gly Ile Leu Ser Gly Phe Asn
            260                 265                 270

Lys Thr Val Leu Arg Thr Leu Pro Arg Ser Gly Asn Leu Ile Val Val
            275                 280                 285

Glu Ser Val Leu Met Ala Val Ala Phe Leu Ala Met Leu Leu Val Leu
    290                 295                 300

Gly Leu Cys Gly Ala Ala Tyr Arg Pro Thr Glu Ile Asp Leu Arg
305                 310                 315                 320

Ser Val Gly Trp Gly Asn Ile Phe Gln Leu Pro Phe Lys His Val Arg
                325                 330                 335

Asp Tyr Arg Leu Arg His Leu Val Pro Phe Phe Ile Tyr Ser Gly Phe
            340                 345                 350

Glu Val Leu Phe Ala Cys Thr Gly Ile Ala Leu Gly Tyr Gly Val Cys
            355                 360                 365

Ser Val Gly Leu Glu Arg Leu Ala Tyr Leu Leu Val Ala Tyr Ser Leu
    370                 375                 380

Gly Ala Ser Ala Ala Ser Leu Leu Gly Leu Leu Gly Leu Trp Leu Pro
385                 390                 395                 400

Arg Pro Val Pro Leu Val Ala Gly Ala Gly Val His Leu Leu Leu Thr
                405                 410                 415
```

-continued

```
Phe Ile Leu Phe Phe Trp Ala Pro Val Pro Arg Val Leu Gln His Ser
                420                 425                 430

Trp Ile Leu Tyr Val Ala Ala Leu Trp Gly Val Gly Ser Ala Leu
            435                 440                 445

Asn Lys Thr Gly Leu Ser Thr Leu Leu Gly Ile Leu Tyr Glu Asp Lys
        450                 455                 460

Glu Arg Gln Asp Phe Ile Phe Thr Ile Tyr His Trp Trp Gln Ala Val
465                 470                 475                 480

Ala Ile Phe Thr Val Tyr Leu Gly Ser Ser Leu His Met Lys Ala Lys
                485                 490                 495

Leu Ala Val Leu Leu Val Thr Leu Val Ala Ala Val Ser Tyr Leu
            500                 505                 510

Arg Met Glu Gln Lys Leu Arg Arg Gly Val Ala Pro Arg Gln Pro Arg
        515                 520                 525

Ile Pro Arg Pro Gln His Lys Val Arg Gly Tyr Arg Tyr Leu Glu Glu
        530                 535                 540

Asp Asn Ser Asp Glu Ser Asp Ala Glu Gly His Gly Asp Gly Ala
545                 550                 555                 560

Glu Glu Glu Ala Pro Pro Ala Gly Pro Arg Pro Gly Pro Glu Pro Ala
                565                 570                 575

Gly Leu Gly Arg Arg Pro Cys Pro Tyr Glu Gln Ala Gln Gly Gly Asp
            580                 585                 590

Gly Pro Glu Glu Gln
            595

<210> SEQ ID NO 27
<211> LENGTH: 606
<212> TYPE: PRT
<213> ORGANISM: Homo sapiens

<400> SEQUENCE: 27

Met Pro Tyr Glu Ile Lys Lys Val Phe Ala Ser Leu Pro Gln Val Glu
1               5                   10                  15

Arg Gly Val Ser Lys Ile Ile Gly Gly Asp Pro Lys Gly Asn Asn Phe
            20                  25                  30

Leu Tyr Thr Asn Gly Lys Cys Val Ile Leu Arg Asn Ile Asp Asn Pro
        35                  40                  45

Ala Leu Ala Asp Ile Tyr Thr Glu His Ala His Gln Val Val Val Ala
    50                  55                  60

Lys Tyr Ala Pro Ser Gly Phe Tyr Ile Ala Ser Gly Asp Val Ser Gly
65                  70                  75                  80

Lys Leu Arg Ile Trp Asp Thr Thr Gln Lys Glu His Leu Leu Lys Tyr
                85                  90                  95

Glu Tyr Gln Pro Phe Ala Gly Lys Ile Lys Asp Ile Ala Trp Thr Glu
            100                 105                 110

Asp Ser Lys Arg Ile Ala Val Val Gly Glu Gly Arg Glu Lys Phe Gly
        115                 120                 125

Ala Val Phe Leu Trp Asp Ser Gly Ser Ser Val Gly Glu Ile Thr Gly
    130                 135                 140

His Asn Lys Val Ile Asn Ser Val Asp Ile Lys Gln Ser Arg Pro Tyr
145                 150                 155                 160

Arg Leu Ala Thr Gly Ser Asp Asp Asn Cys Ala Ala Phe Phe Glu Gly
                165                 170                 175

Pro Pro Phe Lys Phe Lys Phe Thr Ile Gly Asp His Ser Arg Phe Val
            180                 185                 190
```

```
Asn Cys Val Arg Phe Ser Pro Asp Gly Asn Arg Phe Ala Thr Ala Ser
        195                 200                 205

Ala Asp Gly Gln Ile Tyr Ile Tyr Asp Gly Lys Thr Gly Glu Lys Val
    210                 215                 220

Cys Ala Leu Gly Gly Ser Lys Ala His Asp Gly Gly Ile Tyr Ala Ile
225                 230                 235                 240

Ser Trp Ser Pro Asp Ser Thr His Leu Leu Ser Ala Ser Gly Asp Lys
                245                 250                 255

Thr Ser Lys Ile Trp Asp Val Ser Val Asn Ser Val Val Ser Thr Phe
                260                 265                 270

Pro Met Gly Ser Thr Val Leu Asp Gln Gln Leu Gly Cys Leu Trp Gln
            275                 280                 285

Lys Asp His Leu Leu Ser Val Ser Leu Ser Gly Tyr Ile Asn Tyr Leu
        290                 295                 300

Asp Arg Asn Asn Pro Ser Lys Pro Leu His Val Ile Lys Gly His Ser
305                 310                 315                 320

Lys Ser Ile Gln Cys Leu Thr Val His Lys Asn Gly Lys Ser Tyr
                325                 330                 335

Ile Tyr Ser Gly Ser His Asp Gly His Ile Asn Tyr Trp Asp Ser Glu
            340                 345                 350

Thr Gly Glu Asn Asp Ser Phe Ala Gly Lys Gly His Thr Asn Gln Val
        355                 360                 365

Ser Arg Met Thr Val Asp Glu Ser Gly Gln Leu Ile Ser Cys Ser Met
    370                 375                 380

Asp Asp Thr Val Arg Tyr Thr Ser Leu Met Leu Arg Asp Tyr Ser Gly
385                 390                 395                 400

Gln Gly Val Val Lys Leu Asp Val Gln Pro Lys Cys Val Ala Val Gly
                405                 410                 415

Pro Gly Gly Tyr Ala Val Val Cys Ile Gly Gln Ile Val Leu Leu
            420                 425                 430

Lys Asp Gln Arg Lys Cys Phe Ser Ile Asp Asn Pro Gly Tyr Glu Pro
        435                 440                 445

Glu Val Val Ala Val His Pro Gly Gly Asp Thr Val Ala Ile Gly Gly
    450                 455                 460

Val Asp Gly Asn Val Arg Leu Tyr Ser Ile Leu Gly Thr Thr Leu Lys
465                 470                 475                 480

Asp Glu Gly Lys Leu Leu Glu Ala Lys Gly Pro Val Thr Asp Val Ala
                485                 490                 495

Tyr Ser His Asp Gly Ala Phe Leu Ala Val Cys Asp Ala Ser Lys Val
            500                 505                 510

Val Thr Val Phe Ser Val Ala Asp Gly Tyr Ser Glu Asn Asn Val Phe
        515                 520                 525

Tyr Gly His His Ala Lys Ile Val Cys Leu Ala Trp Ser Pro Asp Asn
    530                 535                 540

Glu His Phe Ala Ser Gly Gly Met Asp Met Met Val Tyr Val Trp Thr
545                 550                 555                 560

Leu Ser Asp Pro Glu Thr Arg Val Lys Ile Gln Asp Ala His Arg Leu
                565                 570                 575

His His Val Ser Ser Leu Ala Trp Leu Asp Glu His Thr Leu Val Thr
            580                 585                 590

Thr Ser His Asp Ala Ser Val Lys Glu Trp Thr Ile Thr Tyr
        595                 600                 605
```